(12) United States Patent
Clofent-Sanchez et al.

(10) Patent No.: US 9,782,501 B2
(45) Date of Patent: Oct. 10, 2017

(54) ANTIBODIES FOR MOLECULAR IMAGING OF VULNERABLE PLAQUES IN ATHEROSCLEROSIS

(71) Applicants: Centre National De La Recherche Scientifique, Paris (FR); Universite Bordeaux Segalen, Brodeaux (FR)

(72) Inventors: Gisele Clofent-Sanchez, Le Pian Medoc (FR); Kamel Deramchia, Gradignan (FR); Marie-Josée Joacobin-Valat, St Morillon (FR); Stephane Bonetto, Antibes (FR); Jeanny Traineau, Saint Aubin de Medoc (FR)

(73) Assignees: Centre National De La Recherche Scientifique (CNRS) (FR); Universite Bordeaux Segalen (FR)

( * ) Notice: Subject to any disclaimer, the term of this patent is extended or adjusted under 35 U.S.C. 154(b) by 333 days.

(21) Appl. No.: 14/358,411

(22) PCT Filed: Nov. 15, 2012

(86) PCT No.: PCT/EP2012/072787
§ 371 (c)(1),
(2) Date: May 15, 2014

(87) PCT Pub. No.: WO2013/072438
PCT Pub. Date: May 23, 2013

(65) Prior Publication Data
US 2014/0328753 A1 Nov. 6, 2014

(30) Foreign Application Priority Data
Nov. 15, 2011 (WO) .................. PCT/IB2011/003011

(51) Int. Cl.
*C07K 16/18* (2006.01)
*A61K 51/10* (2006.01)
*A61K 49/00* (2006.01)
*A61K 49/16* (2006.01)

(52) U.S. Cl.
CPC ...... *A61K 51/1093* (2013.01); *A61K 49/0002* (2013.01); *A61K 49/16* (2013.01); *C07K 16/18* (2013.01); *C07K 2317/21* (2013.01); *C07K 2317/622* (2013.01)

(58) Field of Classification Search
None
See application file for complete search history.

(56) References Cited

FOREIGN PATENT DOCUMENTS

| FR | WO 2013072714 A1 * | 5/2013 | ............. C07K 16/18 |
|---|---|---|---|
| WO | 94/25053 A1 | 11/1994 | |
| WO | 2004/107368 A2 | 12/2004 | |
| WO | 2006/093973 A2 | 9/2006 | |

OTHER PUBLICATIONS

Deramchia et al., Am J Pathol. Jun. 2012;180(6):2576-89. doi: 10.1016/j.ajpath.2012.02.013. Epub Apr. 17, 2012.*
Jan. 17, 2013 (WO) International Search Report—App PCT/EP2012/072787.
Shaw, Peter X, et al., "Human-derived anti-oxidized LDL autoantibody blocks uptake of oxidized LDL by macrophages and localizes to atherosclerotic lesions in vivo", Arteriosclerosis, Thrombosis, and Vascular Biology, Lippincott Williams & Wilkins, US, vol. 21, No. 8, Aug. 1, 2001, pp. 1333-1339.
Tsimikas, Soririos, "Noninvasive imaging of oxidized low-density lipoprotein in atherosclerotic plaques with tagged oxidation-specific antibodies," The American Journal of Cardiology, vol. 90, No. 1 OC, Nov. 21, 2002, pp. 22L-27L.
Briley-Saebo, KC, et al., "Targeted Iron Oxide Particles for In Vivo Magnetic Resonance Detection of Atherosclerotic Lesions With Antibodies Directed to Oxidation-Specific Epitopes", Journal of the American College of Cardiology, Elsevier, New York, NY, US, vol. 57, No. 3, Jan. 18, 2011, pp. 337-347.
Gamble W., "Atherosclerosis: the carbonic anhydrase, carbon dioxide, calcium concerted theory" Journal of Theoretical Biology 239, 16-21, 2006.
Philibert P. et al., "A focused antibody library for selecting scFvs expressed at high levels in the cytoplasm," BMC Biotechnology, Nov. 22, 2007, retrieved from http://www.biomedcentral.com/1472-6750/7/81, 17 pages.
Oksala N. et al., "Carbonic anhydrases II and XII are up-regulated in osteoclast-like cells in advanced human atherosclerotic plaques-Tampere Vascular Study," Annals of Medicine, Mar. 23, 2010, 42: pp. 360-370.
Matter CM et al., "Molecular Imagin of Atheroxclerotic Plaques Using a Human Antibody Against the Extra-Domain B of Fibronectin," Circulation Research 2004, 95, retrieved from http://circres.ahajournals.org/content/95/12/1225, pp. 1225-1233.
Deramchia et al. "By-Passing Large Screening Experiments Using Sequencing as a Tool to Identify scFv Fragments Targeting Atherosclerotic Lesions in a Novel In Vivo Phage Display Selection". Int. J. Mol. Sci. 2012, 13, 6902-6923; doi:10.3390/ijms13066902.

* cited by examiner

*Primary Examiner* — Michael Szperka
(74) *Attorney, Agent, or Firm* — Banner & Witcoff, Ltd.

(57) ABSTRACT

Antibodies for molecular imaging of vulnerable plaques in atherosclerosis Antibody specifically binding to atherosclerosis lesions for in vivo imaging and methods for in vivo imaging of atherosclerosis lesions in a patient.

28 Claims, 6 Drawing Sheets

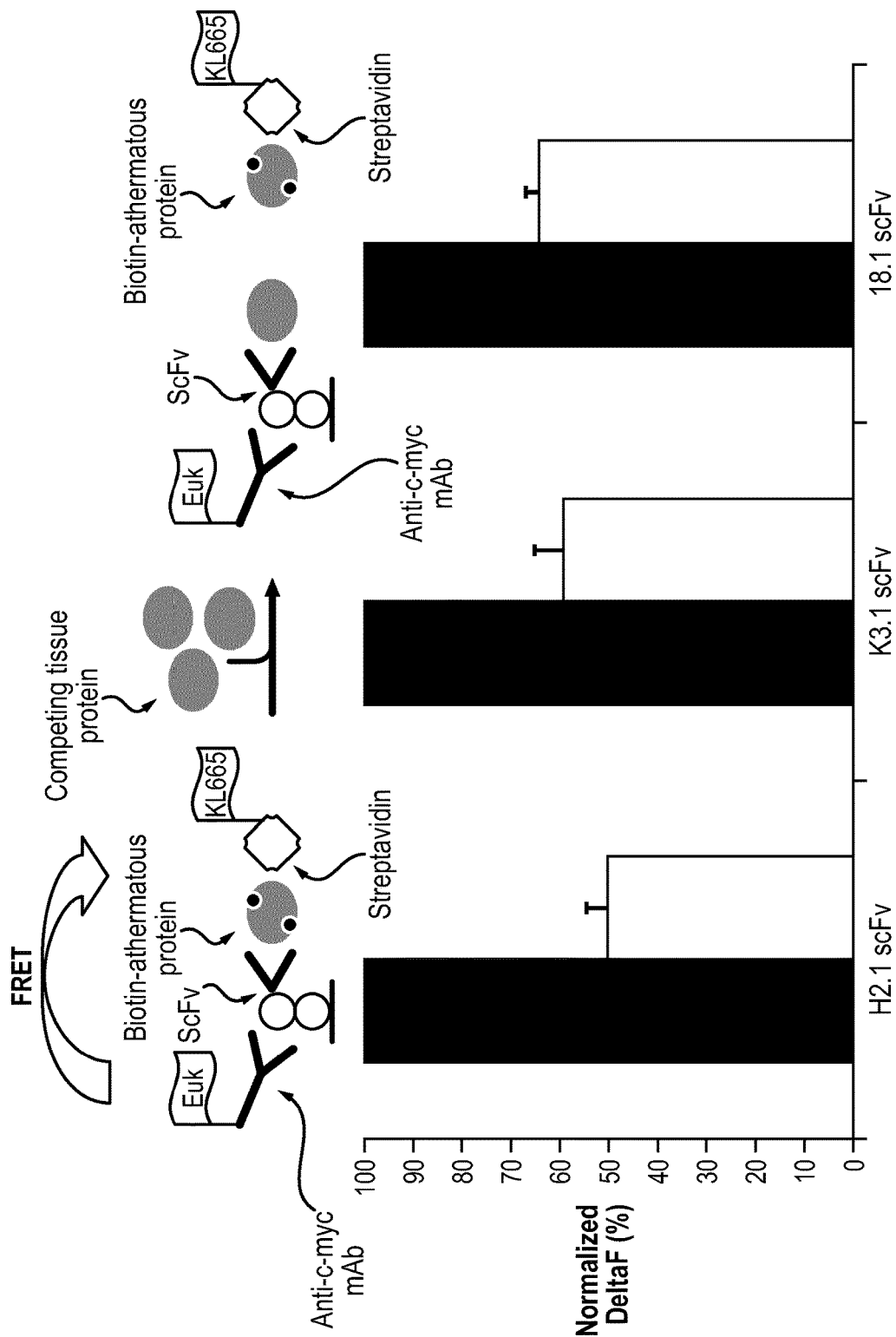

Figure 1:
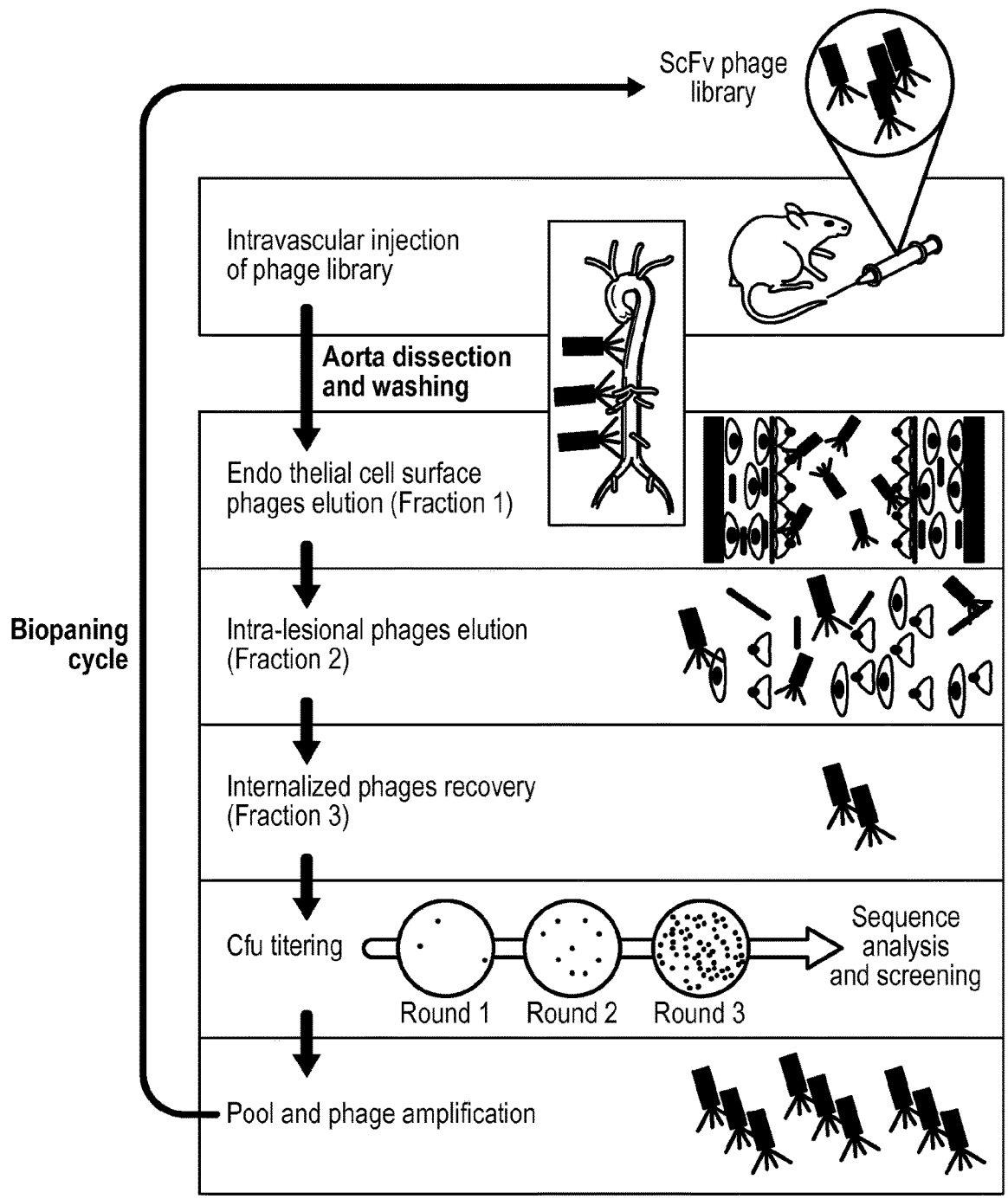

ANTIBODIES FOR MOLECULAR IMAGING OF VULNERABLE PLAQUES IN ATHEROSCLEROSIS

RELATED APPLICATION DATA

This application is a National Stage Application under 35 U.S.C. 371 of co-pending PCT application PCT/EP2012/072787 designating the United States and filed Nov. 15, 2012; which claims the benefit of PCT application number PCT/IB2011/003011, filed Nov. 15, 2011 each of which are hereby incorporated by reference in their entireties.

The present invention relates to antibodies specifically targeting atherosclerotic lesions in vivo.

Epidemiological studies have established that elevated plasma levels of apolipoprotein B-containing lipoproteins in human increase the incidence of coronary heart diseases (CHD). Nevertheless, studies on patients developing premature CHD revealed that 48% had cholesterol levels below 200 mg/dl. In addition, in children with familial hypercholesterolemia and with identical high cholesterol levels, one may have a fatal myocardial infarction at age 10 and the other may survive to age 50. Clearly, additional factors may play a key role in atherogenesis because the rate at which atherosclerosis progresses varies considerably irrespective of the plasma cholesterol level. The disease is likely not only due to hypercholesterolemia, but also to other local and systemic risk factors, which may be necessary or sufficient to induce atherosclerotic lesions.

Atherosclerosis imaging and therapy strategies entered a new era at the turn of the century. Emerging imaging modalities based on the architecture and morphology of the vessel wall have pushed back the boundaries for predicting asymptomatic and vulnerable plaques. Furthermore, experimental and clinical studies have suggested that atherosclerosis can be treated by going beyond the common strategy of using cholesterol- and lipid-lowering drugs. Research efforts have focused on the development of new classes of agents able to act locally and to target the atherogenic components involved in plaque rupture, The pathogenesis of artherosclerosis involves numerous molecular components playing a role in local vascular injury, inflammation, oxidative stress as well as vascular calcification. Atherosclerotic lesions are complex structures containing cholesterol, triglycerides, lipids, calcium carbonate albumin, calmodulin, lipoproteins and other proteins but also fibrous connective tissue and infiltrating inflammatory cells. Gamble (2006) observed that the determinant step of the atherogenic process is the calcium precipitation which traps cholesterol in the plaque. Intramural calcium deposition begins as early as the second decade of life, just after fatty streak formation, and its extent follows atherosclerotic plaque development. Oksala et al. (2010) have recently shown that carbonic anhydrases II and XII are up-regulated in osteoclast-like cells in advanced human atherosclerotic plaques. However, the accessibility and amount of these components of the atherosclerotic lesions in in vivo conditions is not known.

Nevertheless, despite progress in understanding the atherogenic molecular basis thus opening horizons for several promising novel targets, new and more efficient targeting agents for the diagnosis and treatment of atherosclerosis are in ever-increasing demand. Antibodies have received considerable attention, due to their ability to recognize their target with both high specificity and affinity. Various murine antibodies have been successfully tested for imaging atherosclerotic lesions developed in animal models of the disease. However, the use of fully human antibodies is mandatory for further clinical applications. A very small number of studies report the development of such antibodies. Shaw et al. (2001) described an antioxidized LDL human autoantibody blocking uptake of oxidized LDL by macrophages and localizing to atherosclerotic lesions in vivo. Briley-Saebo et al. (2011) used these antibodies directed to oxidation specific epitopes for in vivo Magnetic Resonance Detection of atherosclerotic lesions. Another human antibody has been raised against the extra-domain B of fibronectin, a prominent angiogenic component of the atherosclerotic plaque (Matter et al., 2004).

However, these potential targets on atherosclerotic lesions have been determined by identifying the components of atherosclerotic plaques in vitro.

The inventors used a human scFv library to develop a novel in vivo biopanning approach to investigate scFvs able to target the vascular endothelial cell surface proteins and the subendothelial molecular repertoire expressed within atherosclerotic tissues of apolipoprotein E-deficient mouse and New Zealand White (NZW) fed a high cholesterol diet. These animal models cover most of the features of human atherosclerotic lesions and are a valuable tool to study the pathogenesis of atherosclerosis or to develop agents targeting the plaque components in human disease. In such an in vivo selection on an animal model of atherosclerosis, information can be directly gained on bio-accessibility of the targets.

The present invention relates to seven scFvs antibodies (H2.1, K3.1, I8.1, C3.3, A5.31.F1, B2.31.F1, C4.31.F2) capable to recognize rabbit lesional tissue extracts, in a direct TR-FRET binding assay, and to immunostain rabbit and human atherosclerotic tissue sections, underlining the inter-species similarities of the targeted epitopes. One of the selected scFvs, K3.1, was able to immunoprecipitate CA-II protein, a cytosolic enzyme regulating carbon dioxide levels. CA-II protein is involved in dissolution of arterial calcium deposits and closely associated to macrophage-rich areas.

Advantageously, the antibodies of the present invention bind specifically to atherosclerotic lesions in complex in vivo conditions. Advantageously, the antibodies of the present invention bind to targets on the atherosclerotic plaque which are sufficiently abundant and accessible in vivo.

The selected scFvs constitute the basis for developing new clinical tools dedicated to molecular imaging and therapy of human atherosclerosis.

SUMMARY

A first object of the present invention is an antibody specifically binding to atherosclerosis lesions wherein said antibody or antibody fragment comprises at least a VH CDR1 comprising the amino acid sequence of SEQ ID No. 1, a VH CDR2 comprising the amino acid sequence of SEQ ID No. 2, a VL CDR1 comprising the amino acid sequence of SEQ ID No. 3 and a VL CDR2 comprising the amino acid sequence of SEQ ID No. 4; and comprising at least:
  a VH CDR3 comprising the amino acid sequence of SEQ ID No. 5 and a VL CDR3 comprising the amino acid sequence of SEQ ID No. 6, or
  a VH CDR3 comprising the amino acid sequence of SEQ ID No. 10 and a VL CDR3 comprising the amino acid sequence of SEQ ID No. 11, or
  a VH CDR3 comprising the amino acid sequence of SEQ ID No. 15 and a VL CDR3 comprising the amino acid sequence of SEQ ID No. 16, or a VH CDR3 comprising the amino acid sequence of SEQ ID No. 20 and a VL CDR3 comprising the amino acid sequence of SEQ ID No. 21, or a VH CDR3 comprising the amino acid sequence of SEQ ID No. 25 and a VL CDR3 comprising the amino acid sequence of SEQ ID No. 26, or a VH CDR3 comprising the amino acid sequence of SEQ ID No. 30 and a VL CDR3 comprising the amino acid sequence of SEQ ID No. 31, or a VH CDR3 comprising the amino acid sequence of SEQ ID No. 35 and a VL CDR3 comprising the amino acid sequence of SEQ ID No. 36.

Preferably, the antibodies according to the invention comprise at least:

a VH domain comprising the amino acid sequence of SEQ ID No. 7 and a VL domain comprising the amino acid sequence of SEQ ID No. 8, or a VH domain comprising the amino acid sequence of SEQ ID No. 12 and a VL domain comprising the amino acid sequence of SEQ ID No. 13, or a VH domain comprising the amino acid sequence of SEQ ID No. 17 and a VL domain comprising the amino acid sequence of SEQ ID No. 18, or a VH domain comprising the amino acid sequence of SEQ ID No. 22 and a VL domain comprising the amino acid sequence of SEQ ID No. 23, or a VH domain comprising the amino acid sequence of SEQ ID No. 27 and a VL domain comprising the amino acid sequence of SEQ ID No. 28, or a VH domain comprising the amino acid sequence of SEQ ID No. 32 and a VL domain comprising the amino acid sequence of SEQ ID No. 33, or a VH domain comprising the amino acid sequence of SEQ ID No. 37 and a VL domain comprising the amino acid sequence of SEQ ID No. 38.

In preferred embodiments, the antibodies of the present invention are recombinant human IgG, recombinant human Fab'2, recombinant human scFv-Fab'2, recombinant human scFv-Fc or recombinant human scFv antibody.

Advantageously, the antibody according to the present invention is a scFv antibody selected in the group consisting of:
the scFv antibody of SEQ ID No. 9,
the scFV antibody of SEQ ID No. 14,
the scFV antibody of SEQ ID No. 19,
the scFv antibody of SEQ ID No. 24,
the scFv antibody of SEQ ID No. 29,
the scFv antibody of SEQ ID No. 34, and
the scFv antibody of SEQ ID No. 39.

Another object of the present invention is a polynucleotide encoding an antibody as described above and a recombinant host cell comprising such a polynucleotide.

In preferred embodiments, the antibodies of the present invention are labeled for in vivo imaging. In one embodiment, the antibodies are labeled with a radiotracer for Nuclear Imaging. In another embodiment, the antibodies are labeled with a magnetic contrast agent for Magnetic Resonance Imaging.

The present invention is also related to methods for in vivo imaging of atherosclerosis lesions in a patient comprising visualization of the atherosclerosis lesions by detection of a labeled antibody previously administered to the patient wherein the antibody is an antibody according to the present invention.

In the methods of the present invention, the antibody is preferably labeled with a radiotracer and visualization of the atherosclerosis lesions is performed by Nuclear Imaging.

In the methods of the present invention, the antibody is preferably labeled with a contrast agent and visualization of the atherosclerosis lesions is performed by Magnetic Resonance Imaging.

The present invention is also directed to methods for in vivo imaging of atherosclerosis lesions in a patient comprising the following steps:
a) Intravenous injection of an antibody according to the present invention labeled for in vivo imaging into the patient,
b) Visualization of the atherosclerosis lesions by detection of the labeled antibody of step a) in the patient.

Another object of the present invention is a method for in vivo imaging of atherosclerosis lesions in a patient comprising visualization of the atherosclerosis lesions by detection of a labeled antibody previously administered to the patient wherein the antibody is an antibody binding specifically to human carbonic anhydrase II protein.

Sequence Listing

SEQ ID No. 1: K3.1, C3.3, H2.1, I8.1, A5.31.F1, B2.31.F1 and C4.31.F2 antibody VH CDR1
SEQ ID No. 2: K3.1, C3.3, H2.1, I8.1 A5.31.F1, B2.31.F1 and C4.31.F2 antibody VH CDR2
SEQ ID No. 3: K3.1, C3.3, H2.1, I8.1 A5.31.F1, B2.31.F1 and C4.31.F2 antibody VL CDR1
SEQ ID No. 4: K3.1, C3.3, H2.1, I8.1 A5.31.F1, B2.31.F1 and C4.31.F2 antibody VL CDR2
SEQ ID No. 5: K3.1 antibody VH CDR3
SEQ ID No. 6: K3.1 antibody VL CDR3
SEQ ID No. 7: K3.1 antibody VH
SEQ ID No. 8: K3.1 antibody VL
SEQ ID No. 9: K3.1 scFv antibody
SEQ ID No. 10: C3.3 antibody VH CDR3
SEQ ID No. 11: C3.3 antibody VL CDR3
SEQ ID No. 12: C3.3 antibody VH
SEQ ID No. 13: C3.3 antibody VL
SEQ ID No. 14: C3.3 scFv antibody
SEQ ID No. 15: H2.1 antibody VH CDR3
SEQ ID No. 16: H2.1 antibody VL CDR3
SEQ ID No. 17: H2.1 antibody VH
SEQ ID No. 18: H2.1 antibody VL
SEQ ID No. 19: H2.1 scFv antibody
SEQ ID No. 20: I8.1 antibody VH CDR3
SEQ ID No. 21: I8.1 antibody VL CDR3
SEQ ID No. 22: I8.1 antibody VH
SEQ ID No. 23: I8.1 antibody VL
SEQ ID No. 24: I8.1 scFv antibody
SEQ ID No. 25: A5.31.F1 antibody VH CDR3
SEQ ID No. 26: A5.31.F1 antibody VL CDR3
SEQ ID No. 27: A5.31.F1 antibody VH
SEQ ID No. 28: A5.31.F1 antibody VL
SEQ ID No. 29: A5.31.F1 scFv antibody
SEQ ID No. 30: B2.31.F1 antibody VH CDR3
SEQ ID No. 31: B2.31.F1 antibody VL CDR3
SEQ ID No. 32: B2.31.F1 antibody VH
SEQ ID No. 33: B2.31.F1 antibody VL
SEQ ID No. 34: B2.31.F1 scFv antibody
SEQ ID No. 35: C4.31.F2 antibody VH CDR3
SEQ ID No. 36: C4.31.F2 antibody VL CDR3
SEQ ID No. 37: C4.31.F2 antibody VH
SEQ ID No. 38: C4.31.F2 antibody VL
SEQ ID No. 39: C4.31.F2 scFv antibody

DETAILED DESCRIPTION OF THE INVENTION

Atherosclerosis is a systemic, chronic and progressive inflammatory disease that is characterized by the build-up of lipid-rich plaques within the walls of large arteries. This pathology underlies the clinical condition of myocardial infarction, chronic stable angina, stroke and peripheral vascular disease. Until now there has been no effective way to detect the presence of vulnerable plaques in patients before atherosclerosis has reached a relatively advanced stage. Pathological studies indicate that plaques with large lipid cores, thin fibrous cap and inflammatory cell infiltrates might be more likely to rupture, exposing thrombogenic material from the plaque core and precipitating acute coronary events. The recent concept that risk of plaque rupture is more related to plaque content than plaque size has led to a new imperative for molecular imaging.

The present invention relates to antibodies for molecular imaging of vulnerable plaques in atherosclerosis. The isolated human antibodies of the present invention are able to target molecules involved in the development of high-risk atherosclerotic plaques. These antibodies bind specifically to targets on atherosclerotic lesions which are both abundant and accessible under in vivo conditions.

The term "antibody" is used herein in the broadest sense and specifically covers monoclonal antibodies of any isotype such as IgG, IgM, IgA, IgD and IgE, chimeric antibodies, humanized antibodies, human antibodies and antibody fragments.

A typical IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions".

In the present invention, the limits of the framework and complementarity determining regions are defined using the IMGT numbering system (http://www.imgt.org, Lefranc et al. Dev.Comp.Immunol., 27(1):55-77, 2003).

As used herein, "VH" or "VH" refers to the variable region of an immunoglobulin heavy chain of an antibody, including the heavy chain of an Fv, scFv, dsFv, Fab, Fab' or Fab'2 fragment or whole IgG. Reference to "VL" or "VL" refers to the variable region of the immunoglobulin light chain of an antibody, including the light chain of an Fv, scFv, dsFv, Fab, Fab' or Fab'2 fragment or whole IgG.

As used herein, a "chimeric antibody" is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass. Methods for producing chimeric antibodies are known in the art.

The term "humanized antibody", as used herein, refers to a chimeric antibody which contain minimal sequence derived from non-human immunoglobulin. The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by humans, may be produced using several technologies such as resurfacing and CDR grafting. Humanized chimeric antibodies preferably have constant regions and variable regions other than the complementarity determining regions (CDRs) derived substantially or exclusively from the corresponding human antibody regions and CDRs derived substantially or exclusively from a mammal other than a human.

Preferably, the antibodies of the present invention are recombinant human antibodies.

The antibodies of the present invention include both the full length antibodies discussed above, as well as epitope-binding fragments thereof. As used herein, "antibody fragments" include any portion of an antibody that retains the ability to bind to the epitope recognized by the full length antibody, generally termed "epitope-binding fragments."

Examples of antibody fragments include, but are not limited to, Fab, Fab' and Fab'2, Fd, single-chain Fvs (scFv), single-chain antibodies, disulfide-linked Fvs (dsFv), scFv-Fab'2, scFv-Fc and fragments comprising either a VL or VH region. Epitope-binding fragments, including single-chain antibodies, may comprise the variable region(s) alone or in combination with the entirety or a portion of the following: hinge region, CH1, CH2, and CH3 domains.

In a first embodiment, the present invention relates to antibodies specifically binding to atherosclerotic lesions wherein said antibody or antibody fragment comprises at least a VH CDR1 comprising the amino acid sequence of SEQ ID No. 1, a VH CDR2 comprising the amino acid sequence of SEQ ID No. 2, a VL CDR1 comprising the amino acid sequence of SEQ ID No. 3 and a VL CDR2 comprising the amino acid sequence of SEQ ID No. 4; and comprising at least:
  a VH CDR3 comprising the amino acid sequence of SEQ ID No. 5 and a VL CDR3 comprising the amino acid sequence of SEQ ID No. 6, or
  a VH CDR3 comprising the amino acid sequence of SEQ ID No. 10 and a VL CDR3 comprising the amino acid sequence of SEQ ID No. 11, or
  a VH CDR3 comprising the amino acid sequence of SEQ ID No. 15 and a VL CDR3 comprising the amino acid sequence of SEQ ID No. 16, or
  a VH CDR3 comprising the amino acid sequence of SEQ ID No. 20 and a VL CDR3 comprising the amino acid sequence of SEQ ID No. 21, or
  a VH CDR3 comprising the amino acid sequence of SEQ ID No. 25 and a VL CDR3 comprising the amino acid sequence of SEQ ID No. 26, or
  a VH CDR3 comprising the amino acid sequence of SEQ ID No. 30 and a VL CDR3 comprising the amino acid sequence of SEQ ID No. 31, or
  a VH CDR3 comprising the amino acid sequence of SEQ ID No. 35 and a VL CDR3 comprising the amino acid sequence of SEQ ID No. 36.

The limits of the framework and complementarity determining regions are as defined using the IMGT numbering system.

In a preferred embodiment, the present invention is directed to an antibody as described above comprising at least:
  a VH domain comprising the amino acid sequence of SEQ ID No. 7 and a VL domain comprising the amino acid sequence of SEQ ID No. 8, or
  a VH domain comprising the amino acid sequence of SEQ ID No. 12 and a VL domain comprising the amino acid sequence of SEQ ID No. 13, or
  a VH domain comprising the amino acid sequence of SEQ ID No. 17 and a VL domain comprising the amino acid sequence of SEQ ID No. 18, or a VH domain comprising the amino acid sequence of SEQ ID No. 22 and a VL domain comprising the amino acid sequence of SEQ ID No. 23, or a VH domain comprising the amino acid sequence of SEQ ID No. 27 and a VL domain comprising the amino acid sequence of SEQ ID No. 28, or a VH domain comprising the amino acid sequence of SEQ ID No. 32 and a VL domain comprising the amino acid sequence of SEQ ID No. 33, or a VH domain comprising the amino acid sequence of SEQ ID No. 37 and a VL domain comprising the amino acid sequence of SEQ ID No. 38.

Advantageously, the antibody according to the present invention is a human recombinant IgG, a human recombinant Fab'2, a human recombinant scFv, a human scFv-Fab'2 or a human scFv-Fc.

In another preferred embodiment, the present invention relates to a human recombinant scFv selected in the group consisting of:

the scFv antibody of SEQ ID No. 9,
the scFV antibody of SEQ ID No. 14,
the scFV antibody of SEQ ID No. 19,
the scFv antibody of SEQ ID No. 24,
the scFv antibody of SEQ ID No. 29,
the scFv antibody of SEQ ID No. 34, and
the scFv antibody of SEQ ID No. 39.

The K3.1 antibodies of the present invention bind specifically to the carbonic anhydrase II protein corresponding to Genbank entry AAA51909. The terms "K3.1 antibodies" refer to antibodies specifically binding to atherosclerosis lesions through binding to carbonic anhydrase II protein (CA II). Experimental data demonstrates that antibodies binding to CAII also bind in in vivo conditions to atherosclerosis lesions suggesting that CAII is abundant and accessible in atherosclerosis lesions/plaques. In preferred embodiments, the K3.1 antibodies of the present invention comprise the amino acid sequences of SEQ ID Nos. 1-4, more preferably the K3.1 antibodies comprise also the amino acid sequences of SEQ ID Nos. 5-6 and even more preferably the K3.1 antibodies comprise the amino acid sequences of SEQ ID Nos. 7-8. Advantageously, the K3.1 antibodies are scFv antibodies comprising the amino acid sequence of SEQ ID No. 9.

Another object of the present invention is a polynucleotide encoding an antibody as described herein.

The term "polynucleotide" according to the present invention refers to a single strand nucleotide chain or its complementary strand which can be of the DNA or RNA type, or a double strand nucleotide chain which can be of the cDNA (complementary) or genomic DNA type. Preferably, the polynucleotides of the invention are of the DNA type, namely double strand DNA. The term "polynucleotide" also refers to modified polynucleotides.

The polynucleotides of this invention are isolated or purified from their natural environment. Preferably, the polynucleotides of this invention can be prepared using conventional molecular biology techniques such as those described by Sambrook et al. (Molecular Cloning: A Laboratory Manual, 1989) or by chemical synthesis.

The invention also relates to vectors comprising a polynucleotide as described herein. Preferred vectors include expression vectors for the expression and production of antibodies as described herein.

The invention also relates to recombinant host cells transformed with a polynucleotide as described herein. The man skilled in the art is well aware of the standard methods for incorporation of a polynucleotide into a host cell, for example transfection, lipofection, electroporation, microinjection, viral infection, thermal shock, transformation after chemical permeabilisation of the membrane or cell fusion. Preferred recombinant host cells include transformed bacteria such as E. coli, insect cells, yeasts and mammalian cells such as CHO cells and more preferably recombinant host cells expressing an scFv antibody as described herein.

The antibodies as described herein are preferably for use in medical diagnostic for in vivo imaging of atherosclerosis lesions or atherosclerosis plaques.

The antibodies as described herein are preferably labeled for in vivo medical imaging. Once adequately labeled the antibodies of the present invention may be used in any in vivo medical imaging method.

The terms "Medical imaging" refer to any technique, method or process used to produce images of the human body for medical purposes. Preferred medical imaging techniques include MRI (Magnetic resonance imaging) and Nuclear Imaging.

In a preferred embodiment, the antibodies as described herein are labeled with a radiotracer. A radiotracer is typically a substance containing a radioisotope that allows for easy detection and measurement. A number of different forms of hydrogen, carbon, phosphorous, sulfur and iodine are commonly used in medical diagnostics. The antibodies of the present invention may be labeled with any suitable radiotracer. Preferred radiotracers include radiotracers for medical imaging. Common radiotracers used include $^{18}$F, $^{67}$Ga, $^{81m}$Kr, $^{82}$Rb, $^{99m}$Tc, $^{111}$In, $^{123}$I, $^{131}$I, $^{133}$Xe, $^{201}$Tl and $^{90}$Y. Preferably, the antibodies as described herein are labeled with $^{18}$F, $^{123/131}$I, $^{111}$In, $^{90}$Y or $^{99m}$Tc. Preferably, the antibodies of the present invention are labeled with a radiotracer for Nuclear Imaging.

The antibodies of the present invention may also be labeled with fluorescent probes.

In another preferred embodiment, the antibodies as described herein are labeled with a contrast agent. A contrast agent is a substance used to increase or modify the contrast of organs, fluids or anatomical structures in the human or animal body. The antibodies of the present invention may be labeled with any suitable contrast agent. Preferred contrast agents include contrast agents for medical imaging. Preferably, the antibodies of the present invention are labeled with an MRI (magnetic resonance imaging) contrast agent such as a superparamagnetic contrast agent or a paramagnetic contrast agent. MRI contrast agents are typically chelated metals or colloids. The most commonly used contrast agents include gadolinium (Gd) based contrast agents such as gadolinium-DTPA, iron oxide based contrast agents such as superparamagnetic Small Particles of Iron Oxide (SPIO) and superparamagnetic Ultrasmall Small Particles of Iron Oxide (USPIO) and paramagnetic contrast agents based on manganese chelates such as Mn-DPDP.

In preferred embodiments, the antibodies as described herein are labeled with gadolinium-DTPA, SPIO, USPIO or VUSPIO (Versatile USPIO, WO2004107368 "Ferrofluids stable in neutral media and ferrofluids employing surface-modified particles" Etienne Duguet; Stéphan Mornet; Joseph Pother).

Advantageously, the antibodies of the present invention are labeled with a magnetic contrast agent for Magnetic Resonance Imaging.

The present invention also encompasses medical imaging methods for detection, diagnosis and examination of atherosclerosis lesions.

The present invention encompasses methods for in vivo imaging of atherosclerosis lesions in a patient comprising visualization of the atherosclerosis lesions by detection of a labeled antibody as described herein previously administered to the patient.

The present invention is also related to methods for in vivo imaging of atherosclerosis lesions in a patient comprising visualization of the atherosclerosis lesions by detection of a labeled antibody previously administered to the patient wherein the antibody is an antibody binding specifically to human carbonic anhydrase II protein. More specifically, the antibody binds to human carbonic anhydrase II protein corresponding to Genbank entry AAA51909.

The present invention also encompasses methods for in vivo imaging of atherosclerosis lesions in a patient comprising the following steps:
 a) Administration of an antibody as described herein labeled for in vivo imaging to the patient,
 b) Visualization of the atherosclerosis lesions by detection of the labeled antibody of step a) in the patient.

The present invention also encompasses methods for in vivo imaging of atherosclerosis lesions in a patient comprising the following steps:
 a) Intravascular injection of an antibody as described herein labeled for in vivo imaging into the patient,
 b) Visualization of the atherosclerosis lesions by detection of the labeled antibody of step a) in the patient.

The present invention also encompasses methods for in vivo imaging of atherosclerosis lesions in a patient comprising the following steps:
 a) Intravenous injection of an antibody as described herein labeled for in vivo imaging into the patient,
 b) Visualization of the atherosclerosis lesions by detection of the labeled antibody of step a) in the patient.

Any of the antibodies described herein may be used in the methods of the present invention.

In a preferred embodiment, the methods of the present invention use a labeled K3.1 antibody as described herein which specifically binds to carbonic anhydrase II of Genbank accession No. AAA51909.

The patient is typically a human or animal patient suffering from atherosclerosis or suspected of suffering from atherosclerosis.

The labeled antibody may be administered to the patient via any suitable route. The labeled antibody may be administered by injection into the vascular system or by injection into an organ. Preferred administration routes include parenteral, intravascular and/or intravenous injection. In a preferred embodiment, the labelled antibodies are administered intravenously as a bolus or by continuous infusion over a period of time.

After administration to the patient, adequate time is provided, for distribution of the labeled antibody in the patient. Typically, the labeled antibody is injected intravascular or intravenously in the blood circulation and distributes via the blood circulation in the vascular system of the patient.

The labeled antibody binds specifically to atherosclerotic lesions or plaques in an in vivo environment in the patient and is detected or visualized by any appropriate in vivo imaging technique.

Any suitable in vivo imaging technique may be used in the methods of the present invention.

Preferred imaging techniques include Nuclear imaging methods using the properties of isotopes to visualize labeled antibodies bound to atherosclerosis lesions. Suitable nuclear imaging methods include scintigraphy, PET (positron emission tomography) and SPECT (Single Photon Emission Computed Tomography).

In preferred methods of the present invention, the antibody is labeled with a radiotracer and visualization of the atherosclerosis lesions is performed by Nuclear Imaging.

Another preferred imaging technology used in the methods of the present invention is Magnetic Resonance Imaging. Any suitable MRI technique may be used in the methods of the present invention.

In preferred methods of the present invention the antibody is labeled with a contrast agent and visualization of the atherosclerosis lesions is performed by Magnetic Resonance Imaging.

Another object of the present invention is an antibody as described herein, preferably a labeled antibody, for use in in vivo diagnostic of atherosclerosis lesions in a patient comprising administration of the antibody into the patient and visualization of the antibody bound to atherosclerotic lesions.

Another object of the present invention is an antibody as described above for use in therapy. Preferably, the antibodies of the present invention are for use in the treatment of atherosclerosis.

Another object of the present invention is an antibody as described herein for use in drug delivery. Preferably, the antibodies of the present invention are for use in targeting therapeutic agents to atherosclerotic lesions.

The present invention also encompasses a pharmaceutical composition comprising an antibody as described herein. The present invention provides pharmaceutical compositions comprising:
 a) an effective amount of an antibody as described herein, and
 b) a pharmaceutically acceptable carrier, which may be inert or physiologically active.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20.

The pharmaceutical compositions encompassed by the present invention may also contain a therapeutic agent for the treatment of atherosclerosis. In preferred embodiments the antibodies of the present invention are used for drug delivery to atherosclerotic plaques.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperinoneal, subcutaneous). In a preferred embodiment, the compositions of the invention are administered intravenously as a bolus or by continuous infusion over a period of time.

The invention is also related to the use of an antibody as described herein for the manufacture of a medicament for the treatment of atherosclerosis.

The present invention also provides methods for treating atherosclerosis including administering an effective amount of an antibody as described herein to a human or to a patient in need thereof.

FIGURES

FIG. 1. In vivo selection protocol scheme. ScFv phage library was intravenously injected into the ApoE$^{-/-}$ mouse model and allowed to circulate for 3 times 5 minutes. The aorta was then removed and unbound phages washed out. Sequential recovery of bound phages was performed from vascular surface (F1), subjacent tissue (F2) and in-cell compartment (F3). A sample from each fraction was used to generate a new selected library for the next round of biopanning. This process was repeated three times, whereas from the second and third round, random scFv clones were sequenced and selected for future screening.

Figure 2:
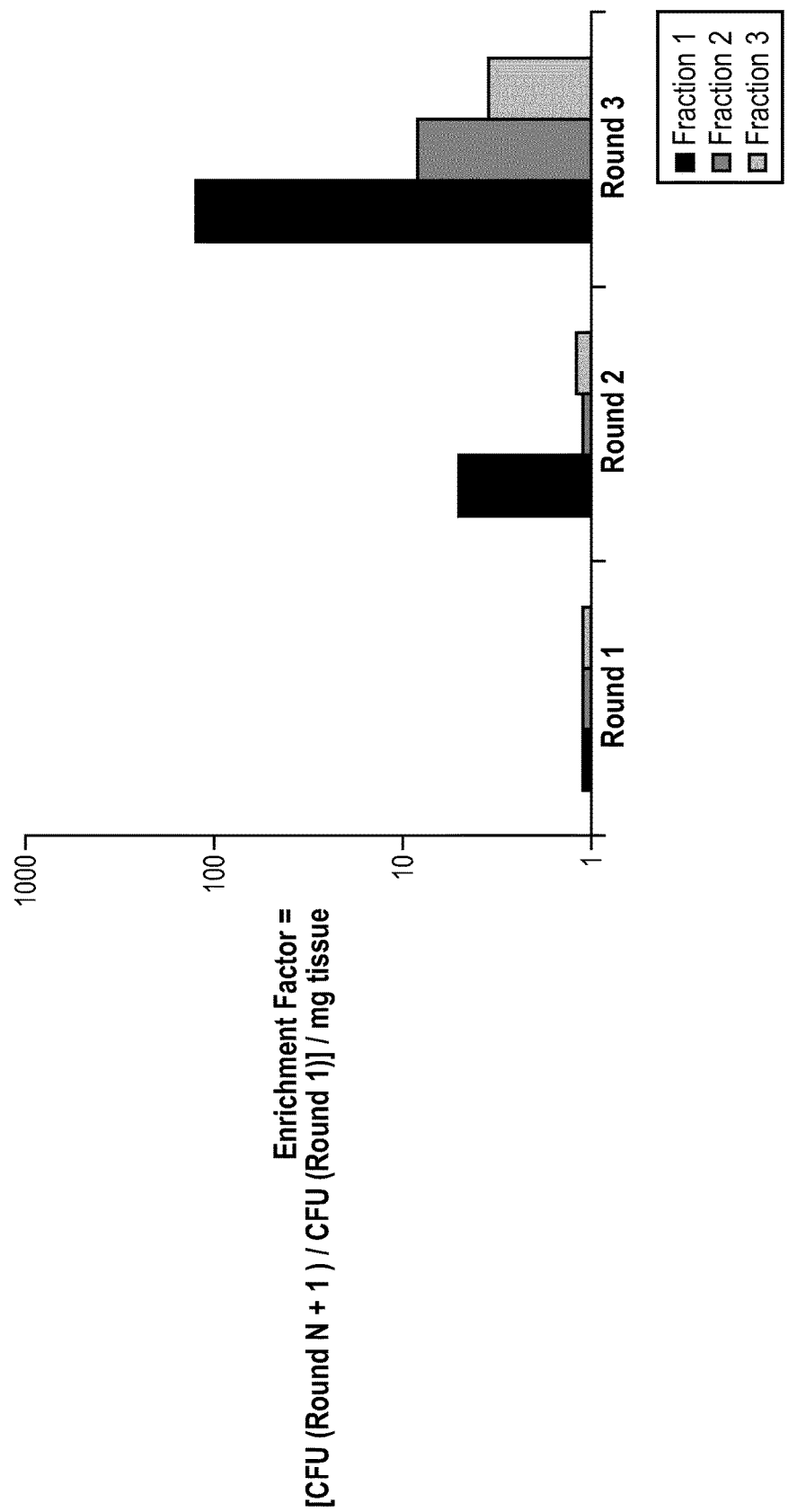

FIG. 2. Phage enrichment after three rounds of in vivo biopanning. The number of phages recovered (cfu, colony forming units) from round n+1 was determined relative to the number of cfu obtained from the round 1 per mg of tissue. F1, F2 and F3 fractions respectively correspond to phages rescued from vascular surface and subjacent tissue or internalized.

Figure 3:
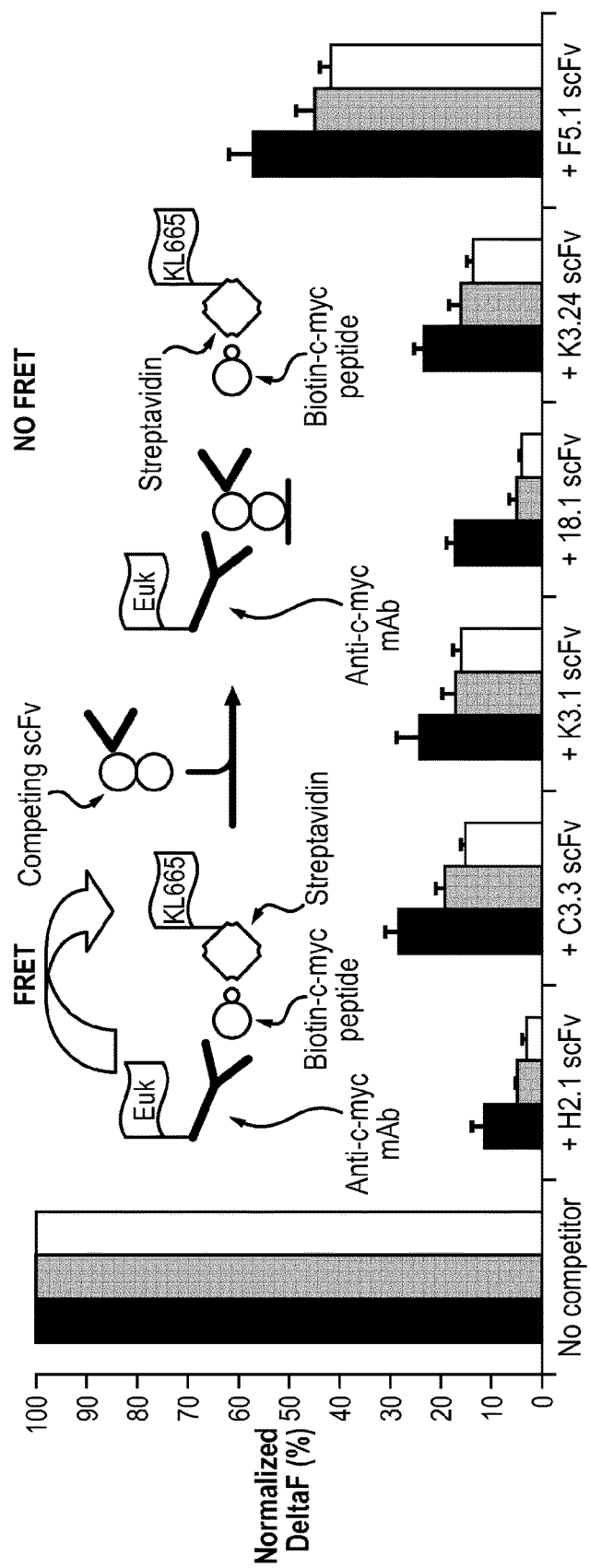

FIG. 3. Inhibition of HTRF biotin-c-myc peptide sandwich signal. HTRF sandwich assay principle is depicted at the top. The donor fluorophore europium cryptate (Eu)K conjugated to anti-c-myc mAb was able to recognize c-myc tag of biotinylated peptide. The acceptor fluorophore XL665 conjugated to streptavidin bound biotinylated amino acids of c-myc peptide. In the absence of competitors, a FRET sandwich signal generated by the biotin-c-myc peptide is recorded. Competition with scFvs for the c-myc tag abolished the FRET signal. The signals were measured in the presence of 0.4 nmol/L of mAb-(Eu)K, 1.25 nmol/L of streptavidin-XL665 and 5 nmol/L of biotin c-myc peptide. Five microliter of competitor were added in each well, corresponding to a final concentration between 5 and 170 nmol/L according to the scFv clone production and purification. Specific HTRF signal was measured as a percentage DeltaF (percent DeltaF) and normalized with regard to the maximum signal in the absence of competitor (taken as 100%). The time course of competition was measured after 6 hours (■), 16 hours (▩) and 24 hours (□) of incubation at 4° C. Histobar values represent the average of at least three independent experiments±SD performed from the same purified scFv production.

Figure 4:
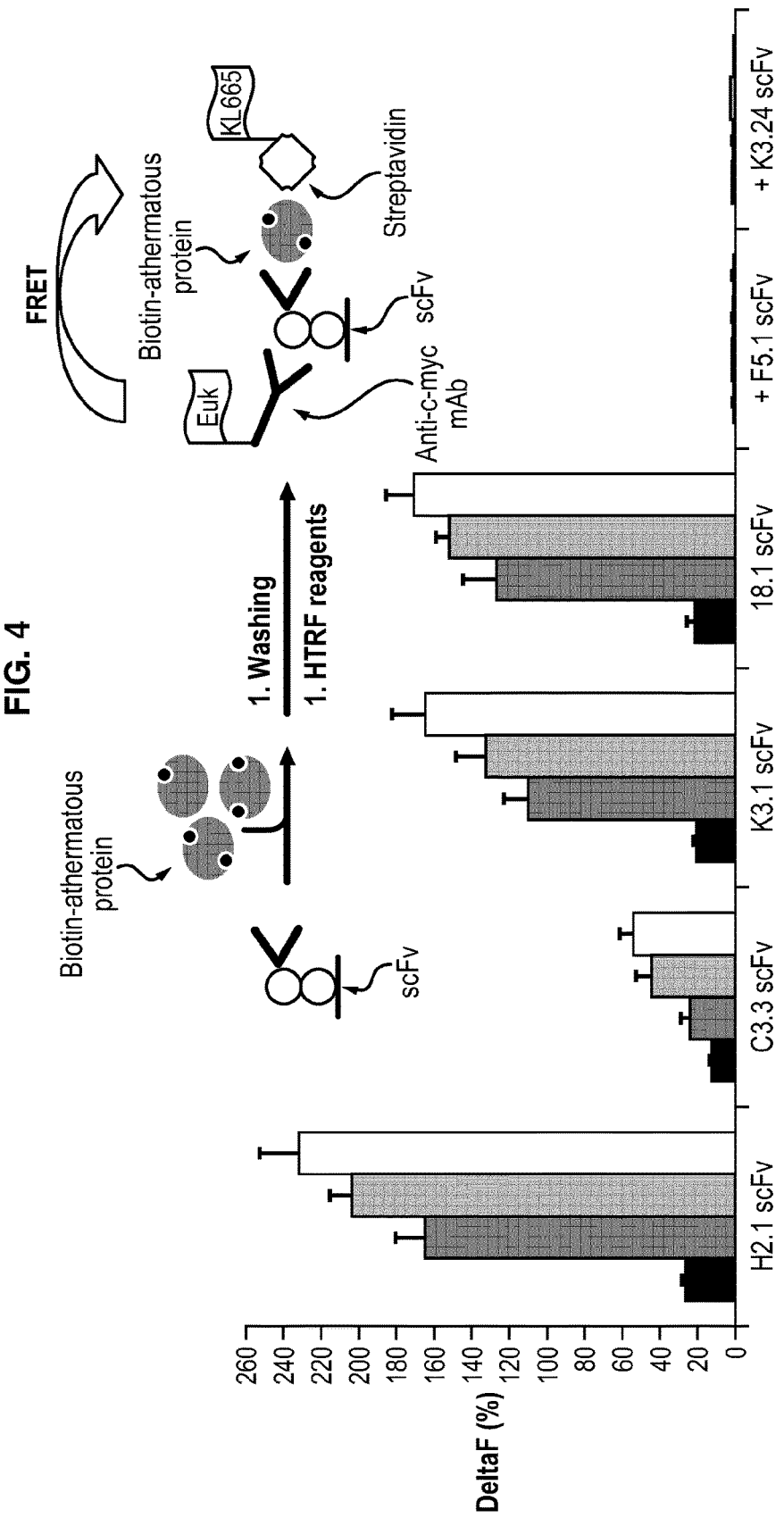

FIG. 4. Direct TR-FRET binding assays between scFvs and atheromatous tissue extracts. Direct TR-FRET principle is schematized at the top. The donor fluorophore europium cryptate (Eu)K conjugated to anti-c-myc mAb was able to recognize c-myc tag expressed by scFvs. The acceptor fluorophore XL665 conjugated to streptavidin bound biotinylated protein extract. When scFvs and target proteins bound, a FRET signal was recorded. Excitation of the donor at 320 nm resulted in the fluorescence resonance transfer to the acceptor at 620 nm, leading to the emission of the acceptor at 665 nm. Specific TR-FRET signal was measured as a percentage DeltaF (percent DeltaF). The time course of the detection of the complex formation was performed after 6 hours (■), 16 hours (▩), 24 hours (□) and 40 hours (□) of incubation at 4° C. Ten microliter of scFv were coated on the plate at concentrations between 3 and 10 μg/mL according to the clone. The signals were measured in the presence of 4 nmol/L of mAb-(Eu)K, 4 nmol/L of streptavidin-XL665, and 30 μg/mL of biotinylated atheromatous protein extract or 50 μg/mL of biotinylated BSA (data not shown). Histobar values represent the average of at least three independent experiments±SD performed from the same purified scFv production.

Figure 5A:
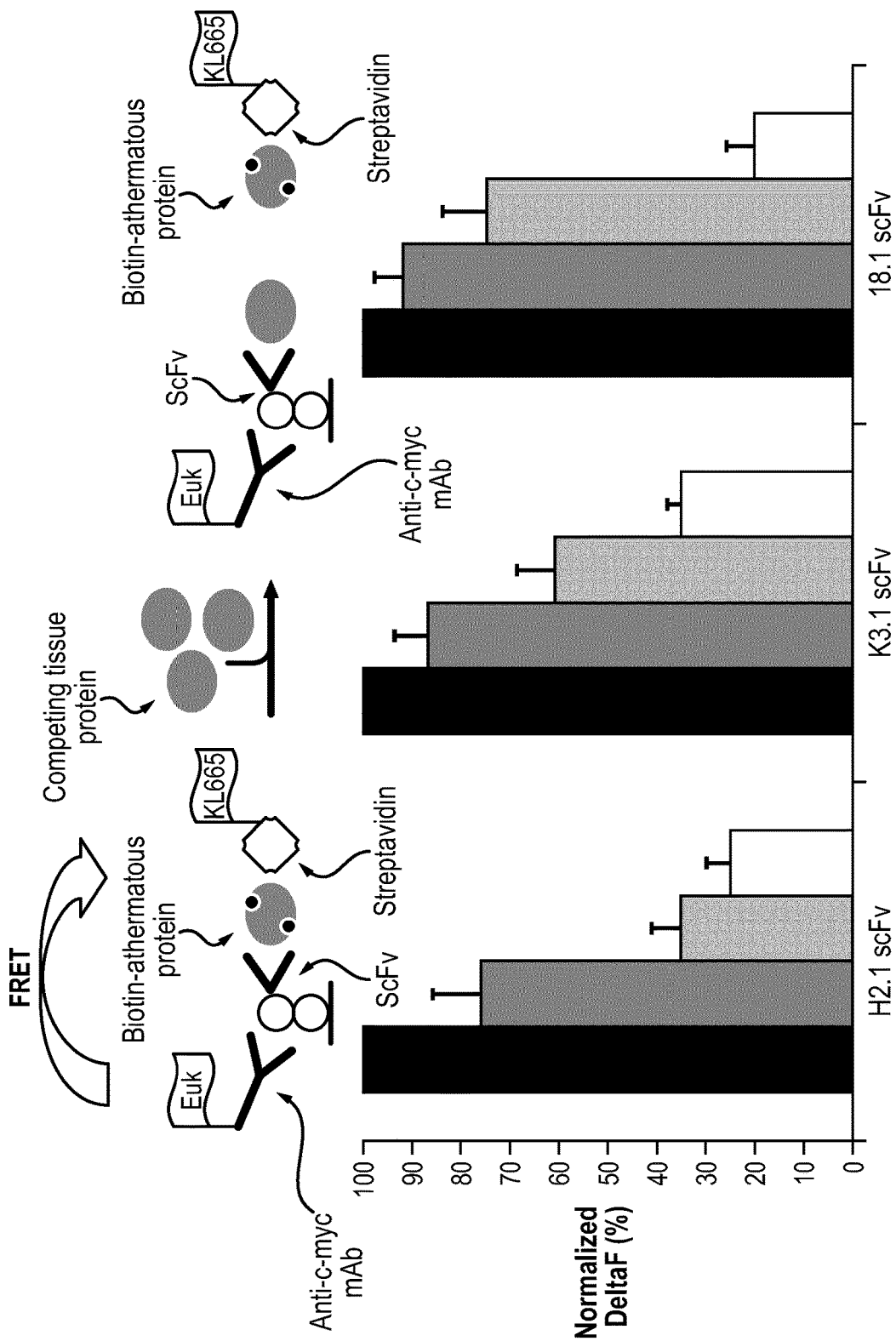

FIGS. 5A and 5B. Inhibition of direct TR-FRET binding assays with unlabeled tissue extracts. Direct TR-FRET inhibition principle is depicted at the top of FIG. 5A. The donor fluorophore europium cryptate (Eu)K conjugated to anti-c-myc mAb was able to recognize c-myc tag expressed by scFvs. The acceptor fluorophore XL665 conjugated to streptavidin bound biotinylated atherogenic protein extract. The FRET signal recorded (percent DeltaF) was then measured in the presence of 2.5 (▩), 5 (□), 6 (□) fold excess of unlabeled protein extract from animals submitted to an atherogenic diet (A) and 6 (□) fold excess of unlabeled protein extract from untreated animals (FIG. 5B). Specific TR-FRET signal was measured as a percentage DeltaF (percent DeltaF) and normalized with regard to the signal obtained in the absence of competitor (taken as 100%) (■). Ten microliter of scFv were coated on the plate at concentrations between 3 and 10 μg/mL according to the clone. The signals were measured in the presence of 4 nmol/L of mAb-(Eu)K, 4 nmol/L of streptavidin-XL665, 30 μg/mL of biotinylated atheromatous protein extract and monitored after 16 hours of incubation at 4° C. Histobar values represent the average of at least three independent experiments±SD performed from the same purified scFv production.

EXAMPLES

Materials and Methods
Animal Models (1)

All animal experiments were performed in conformity with the Guide for the Care and Use of Laboratory Animals (NIH Publication No. 85-23, revised 1996) and were accredited by the local ethical committee.

ApoE$^{-/-}$ KO mice were obtained from Charles Rivers Laboratories (St Germain sur l'Arbresle, France). To promote advanced lesions in ApoE$^{-/-}$ mice, animals were fed a high-fat Western diet (0.3% (w/w) cholesterol) for 24 weeks.
Animal Models (2)

All animal experiments were performed in accordance with the Guide for the Care and Use of Laboratory Animals (NIH Publication No. 85-23, revised 1996) and were approved by the local ethics committee. Adult male New Zealand rabbits (NZW), weighting 2.5 to 3.0 kg, were obtained from Charles Rivers Laboratories (St Germain sur l'Arbresle, France). Rabbits were fed a fat atherogenic diet including 0.3% cholesterol. To induce atherosclerosis, two surgeries were performed: The first surgery was performed two months after the beginning of the diet and the second was performed 2 months later to allow the formation of complex plaques with intramural thrombi.

In the first surgery, endothelial cells were removed with a specially designed Fogarty catheter (Fogarty 4F; Edwards Lifesciences), a catheter with an inflatable balloon near its tip. The Fogarty catheter was introduced over a guide wire with the tip placed at the level of diaphragm. The balloon was inflated and then pulled back to remove endothelial cells from the thoracic until the abdominal aorta. This process was repeated 3 times, and the catheter was removed. Two months later, the same rabbits were subjected to an angioplasty using an expandable latex balloon (Maxxum®, Boston Scientific; 20 mm long, diameter of 4.5 mm) that was firmly pressed against the arterial wall. The balloon for angioplasty was advanced through a femoral arteriotomy to the descendent thoracic aorta under radioscopic guidance. It was inflated every 2 cm from the region of renal arteries to iliac bifurcation. During surgery, rabbits were anesthetized by the concurrent intramuscular injection of 20 mg/kg ketamine and 2 mg/kg xylazin. Anaesthesia was maintained with isoflurane gas (0.25% to 0.35%). As a preventive anti-thrombotic treatment, 1000 UI heparine (Héparine Choay®, Sanofi Synthélabo) was infused. Also administered as an analgesia was 100 mg aspirine (Aspégic® injectable, Sanofi Synthélabo). A skin incision was made and the femoral artery was surgically exposed, the left for the removal of endothelial cells and the right for the angioplasty.

Human Tissue Specimens

Human carotid arteries were collected from carotid endarterectomy. Human coronary arteries were harvested from patients with end-stage heart failure having undergone heart transplantation. All the clinical interventions took place at Haut-Lévèque Hospital (Pessac, France). Human tissue specimens were collected after informed consent. They were immediately processed, frozen at −80° C. or embedded in paraffin.

Human Phage-ScFv Library

A semi-synthetic scFv-fragment library designed and constructed by P. Philibert et al. was used. Briefly, the library was created from a single optimized human scFv framework (13R4 scFv) by introducing amino acid distributions and lengths in the CDR3 the closest to those observed in natural human CDR3 loops. Two sets of 13 VH libraries with CDR3 loops ranging from 5 to 17 amino acids and 5 VL libraries (κ+λ) with CDR3 loops ranging from 9 to 11 amino acids, were then screened for their ability to be expressed in frame with fusion protein CAT (Chloramphenicol acetyltransferase) enzyme on selective media before PCR assembly. The library was constructed in the pCANTAB6 phagemid vector in fusion with the N-terminus of the minor pIII protein. Its diversity is about $1.5 \times 10^9$ different variants.

Atheromatous Protein Extraction and Biotinylation

Aortas from untreated rabbits and balloon-injured aortas from hypercholesterolemic rabbits were extracted from the aortic arch to the iliac bifurcation, washed and fractioned in order to independently solubilize tissue proteins in four different lysis buffers: M-PER (Thermo Fisher Scientific, Brebières, France), T-PER (Thermo Fisher Scientific), low stringent lysis buffer (50 mmol/L HEPES, pH 7.4; 137 mmol/L NaCl; 1% NP-40 (v/v); 2 mmol/L EDTA; 1 mmol/L PMSF; protease inhibitors cocktail (Roche Diagnostics, Meylan, France)) and high stringent lysis buffer (50 mmol/L HEPES, pH 7.4; 150 mmol/L NaCl; 1% (v/v) NP-40; 0.5% (v/v) Triton; 0.5% Na-Deoxycholate; 1 mmol/L EDTA; 1 mmol/L PMSF; protease inhibitors cocktail). Homogenization was performed using first a Polytron TP-20 Homogenizer (Kinematica, Lucerne, Switzerland) and then a sonicator (3×10-second pulses at 80% magnitude). After two centrifugations at 13,000×g for 45 minutes at 4° C. to discard insoluble material from the supernatant, the protein concentration of every soluble extract was determined using the Bradford assay kit according to the manufacturer's instructions (Thermo Fisher Scientific). Proteins from M-PER, T-PER and high stringent lysis buffer extraction were then dialyzed against low stringent lysis buffer for 16 hours at 4° C. and 200 µg from each protein extraction were biotinylated with three different molar ratios of proteins/biotin-XX SSE (Invitrogen, Eragny sur Oise, France): 1:5, 1:10 and 1:20 in 100 mmol/L NaHCO$_3$, pH 8.3 for 30 minutes at 4° C. Excess of reactive biotin was then quenched with 100 mmol/L Glycine, pH 7.4 for 10 minutes at 4° C. and the samples dialyzed against low stringent lysis buffer for 16 hours at 4° C.

In Vivo Biopanning in Atherosclerotic Mouse Model

In vivo phage display selections were performed in ApoE$^{-/-}$ mice. Three bolus of PBS containing $1 \times 10^{12}$ colony-forming units (cfu) were injected into the tail vein for 3 times 5 minutes. The animal was then sacrificed and perfused through the heart with 20 mL of PBS to ensure phage clearance from the blood. The aorta was then extracted from the aortic arch to the iliac bifurcation. The tissue was weighed, gently cut lengthwise and rinsed six times with 500 µL of cold PBS. The endothelium cell surface-bound phages (F1 fraction) were eluted with 100 µL of 0.1 mol/L Glycine-HCl, pH 2.2 for 8 minutes at room temperature under gentle agitation. After centrifugation at 500×g, eluted phages were collected and immediately neutralized with 15 µL of 1 mol/L Tris-HCl, pH 9.1 in a clean tube. Meanwhile, the aorta was washed three times with 300 µL of cold PBS and the washing eluates were then pooled in the previous fraction. To access the intra-tissular phages (F2 fraction), the aorta was dissociated with 900 µL of PBS (Ca$^{2+}$, Mg$^{2+}$ free) containing 2000 U/mL of collagenase type II and adjusted at 1 mL with 2.5% Trypsin-EDTA for 30 minutes at 37° C. under agitation. The solubilizate was vigorously vortexed and centrifuged at 1000×g for 10 minutes at 4° C. The supernatant was recovered and the pellet washed three times with 400 µL of PBS (Ca$^{2+}$, Mg$^{2+}$ free). In addition, 250 µL of 0.1 mol/L Glycine-HCl, pH 2.2 were added to the cell homogenate and incubated for 8 minutes at room temperature under gentle agitation. After centrifugation, eluted phages were collected, neutralized in a clean tube and pooled to the washing eluate. Three supplementary cell washings were then carried out with 250 µL of PBS. Eventually, to access the internalized phages (F3 fraction), the homogenate was incubated with 500 µl of 100 mmol/L triethylamine (TEA), pH 11 for 5 minutes at room temperature by vigorous vortexing. Neutralization was then done by addition of 250 µL of 1M Tris-HCl, pH 7.4. After centrifugation at 1000×g for 10 minutes, the supernatant was collected and the pellet was washed twice more with 500 µL of PBS. Phage fractions were separately rescued by infection of 25 mL of 2×TY medium containing XL1-blue *E. coli* host (Stratagene, La Jola, Calif.) in log-growth phase. After 45 minutes, bacteria were centrifuged and spread onto 2×TY Amp (100 µg/mL)/Glucose (2% (w/v)) agar plates for 16 hours at 30° C. The phage libraries were then produced in 100 mL of 2×TY Amp (100 µg/mL)/Kana (50 µg/mL) following super-infection with M13KO7 helper phage (Invitrogen, Cergy-Pontoise, France) for 16 hours at 25° C. Phages were then purified from the supernatant culture by two precipitations with 0.2 volume of solution containing 20% (w/v) PEG 8000, 2.5 mol/L NaCl. Eventually, the pellet containing phage particles was resuspended in a final volume of 500 µL sterile cold PBS and passed through a 0.22 µm pore-size filter. The titer of each production was around $5 \times 10^{13}$ cfu/mL. Two additional rounds of selection and amplification in subsequent mice were then performed with respectively $1 \times 10^{11}$ and $1 \times 10^{10}$ cfu and carried out as previously described. Plated bacterial clones from the second and third rounds of biopanning were randomly picked for nucleotide sequence analysis (Millegen, Toulouse, France) by using the LMB3 primer (sequence, CAG-GAAACAGCTATGAC SEQ ID No. 40) corresponding to the pCANTAB6 phagemid sequence downstream of the scFv insert. Sequence translation, comparison and alignment were done using IMGT/V-QUEST database (http://imgt.cinesfr/).

In Vivo Biopanning in the Atherosclerotic New Zealand Rabbit Model

A continuous flow (170 µL/min) of PBS containing $1\times10^{13}$ colony-forming units (cfu) of phagemid vector was injected into the marginal ear vein of rabbits for 30 min. The animals were then sacrificed and perfused via the heart with 120 mL of PBS to ensure phage clearance from the blood. The aorta was recovered from the aortic arch to the iliac bifurcation. The tissue was weighed, gently cut along the length and rinsed six times with 1 mL of cold PBS.

The endothelium cell surface-bound phages (fraction F1) were eluted with 950 µL of 0.1M glycine-HCl, pH 2.2 for 8 min at room temperature under gentle agitation. Eluted phages were collected and immediately neutralized with 90 µL of 1M Tris-HCl, pH 9.1 in a clean tube. The aorta was then washed three times with 500 µL of PBS ($Ca^{2+}$, $Mg^{2+}$ free). Washes were pooled and stored at 4° C.

In order to elute intra-tissular phages (fraction F2), the aortic tissue was incubated with 900 µL of PBS ($Ca^{2+}$, $Mg^{2+}$ free) containing 2000 U/mL of collagenase type II (Gibco, France) adjusted to 1 mL with 2.5% Trypsin-EDTA (Eurobio, France) for 30 min at 37° C. with agitation. Dissociated tissue was homogenized with the aid of a Polytron homogenizer (Ultraturax TP-20, Kinematica, Lucerne, Swithzerland) on ice. The homogenate was centrifuged for 10 min at 5000×g to remove insoluble material. This one was homogenized again twice in the same way as tissue aorta. After centrifugation, supernatants containing eluted phages were collected, pooled in a clean tube with a protease-inhibitor cocktail added.

To access to internalized phages (fraction F3), the insoluble material was incubated with 500 µL of 0.1M TEA (Sigma-Aldrich, France) for 5 min at room temperature with vigorous vortexing. Samples were neutralized by addition of 250 µL of 1M Tris-HCl, pH 7.4. After centrifugation at 1000×g for 10 min, the supernatant was collected. Phage fractions F1, F2 and F3 were separately rescued by infection of XL1-blue Escherichia coli (Stratagene, La Jolla, Calif., USA) grown to log phase in 25 mL of 2×TY medium. After 45 min incubation infected bacteria were centrifuged and plated onto plates containing 2×TY with ampicillin (100 µg/mL)/glucose (2% (w/v)) and incubated 16 h at 30° C. The phage libraries were produced following the super-infection with M13KO7 helper phage (Invitrogen, Cergy-Pontoise, France) in 100 mL of 2×TY containing ampicillin (100 µg/mL) and kanamycin (50 µg/mL) for 16 h at 25° C. Phages were then purified from the supernatant culture by precipitation with 0.2 volumes of 20% (w/v) PEG 8000, 2.5 M NaCl. After centrifugation at 11,000×g for 45 min at 4° C., the pellet containing phage particles was resuspended in a final volume of 500 µL sterile cold PBS and passed through a 0.22 µm pore-size filter. The titer of each production was around $3\times10^{13}$ cfu/mL. One additional round of in vivo selection and amplification was performed with $1\times10^{12}$ cfu.

Soluble scFv Production from Bacterial Culture

Selected XL1-blue clones cultured for 5 hours in 500 µL of 2×TY Amp (100 µg/mL)/Glucose (2% (w/v)) in 2 mL Masterblock (Greiner Bio-one, Courtaboeuf, France) were super-infected with M13KO7 helper phage for 45 minutes. After centrifugation and removal of the supernatant, pellets were resuspended in 1 mL of 2×TY Amp (100 µg/mL)/Kana (50 µg/mL) and an aliquot of each culture was spread onto 2×TY Amp/Kana agar plates. Isolated bacterial clones were then incubated for 16 hours in 500 µL of 2× TY Amp/Kana at 25° C. to induce phage production. After two successive centrifugations, 1 µL of phage-containing supernatant was used to infect 20 µL of HB2151 E. coli host (Amersham Pharmacia Biotech, Uppsala, Sweden) in log-growth phase. After 45 minutes, bacteria were plated onto 2×TY Amp (100 µg/mL)/Glucose (2% (w/v)) and incubated for 16 hours at 30° C. Selected HB2151 clones were then cultured in 2×TY Amp (100 µg/mL)/Sucrose (0.4M) until they reached the log-growth phase. After spinning, the scFv production from the bacterial pellet was induced in 50 mL of 2×TY Amp (100 µg/mL)/IPTG (isopropyl-thio-galactoside) (200 mmol/L) for 16 hours at 25° C.

ScFv Purification on Nickel-Affinity Chromatography

Fifty mL of HB2151 cell culture were pelleted by centrifugation and the pellet resuspended in 1:10 (v/v) of ice-cold osmotic choc buffer (1 mol/L Tris-HCl pH 8, 1 mg/mL Lysozyme, 1 mmol/L PMSF, protease inhibitors cocktail (Roche Diagnostics)) for 1 hour at 4° C. on a rotary shaker. Bacterial lysis was then performed by two sonication cycles of 3×10-second pulses at 80% magnitude. After centrifugation at 20,000×g for 30 minutes at 4° C. to remove the insoluble material, 6His-tagged scFvs were purified by immobilized metal affinity chromatography (IMAC) using Ni-NTA resins (Pierce, Bezons, France)[27] and monitored by the Biopilot Chromatographic System (Amersham Biosciences, Saclay, France). Briefly, after equilibration of the column with running buffer (20 mmol/L Tris-HCl, pH 7.0) and sample loading, a two-step elution was performed. The first was achieved in the presence of 25 mmol/L imidazole (pH 7.0) to remove unspecific binding on nickel column, and the second with 250 mmol/L imidazole (pH 7.0) was done to elute nickel-bound scFvs into four to five 1 mL fractions. Each recovered fraction was then evaluated for its protein content by absorption at 280 nm and dialyzed against PBS for 16 hours at 4° C.

TR-FRET scFv Binding Assays

Binding assays between scFvs and atheromatous protein extracts were assessed by direct TR-FRET. Black Fluotrac 600 microplate (Greiner) was coated with 10 µL of scFv (final concentration comprised between 3 and 10 µg/mL according to the clone) in 0.1 mol/L $NaHCO_3$, pH 8.6 for 16 hours at 4° C. Subsequently, plates were blocked for 3 hours at 4° C. using 1% BSA (w/v) in PBS solution. Following washing in PBS, 30 µg/mL of biotinylated atheromatous protein extract in 1% BSA/PBS was incubated for 16 hours at 4° C. After washing in PBS, 50 µL of reaction buffer (100 mmol/L Phosphate buffer, pH 7; 400 mmol/L KF buffer; 0.1% BSA), 4 nmol/L of anti c-myc-(Eu)K (Cisbio Bioassays, Codolet, France) and 4 nmol/L of streptavidin-XL665 (Cisbio Bioassays) were incubated in a final volume of 100 µL. FRET signal emission was measured and monitored with an Infinite® F500 reader (Tecan, Lyon, France) on a 40-hour time course. The percent DeltaF values reported the intensity of the direct binding between scFvs and protein extract. Inhibition assays of the direct TR-FRET binding signal were performed after 16 hours of incubation at 4° C. in the presence of 2.5, 5 and 6 fold excess of unlabeled protein extract from atherogenic animals and 6 fold excess of protein extract from healthy animals. The percent DeltaF values in the presence of unlabeled proteins were normalized relative to the percent DeltaF values in the absence of unlabeled proteins (taken as 100%). Nickel-purified scFv fractions were tested beforehand for their ability to inhibit HTRF® (homogeneous time-resolved fluorescence, Cisbio Bioassays) sandwich emission signal of biotin-c-myc peptide. The reaction was set up in 96-halfwell black plates (Greiner) and in 100 μL of reaction volume containing 50 μL of reaction buffer (100 mmol/L Phosphate buffer, pH 7; 400 mmol/L KF buffer; 0.1% BSA), 0.4 nmol/L of anti c-myc-(Eu)K (Cisbio Bioassays), 5 μL of scFv (final concentration comprised between 5 and 170 nmol/L according to the clone), 1.25 nmol/L of streptavidin-XL665 (Cisbio Bioassays), and 5 nmol/L of biotin-c-myc peptide (Cisbio Bioassays). Fluorescence emission was measured on a 24-hour time course after incubation at 4° C. The percent DeltaF values were normalized using the competitor-free wells percent DeltaF values as the maximal activation (=100%).

The FRET measurements were expressed as the ratio of the emission intensity at 665 nm to that at 620 nm×10,000. The normalized FRET signals were expressed as DeltaF (%)=(Ratio$_{assay}$–Ratio$_{Blank}$)/Ratio$_{Blank}$. For the direct and inhibition binding assays, the blank values were obtained from signals generated in the absence of scFvs coating. For the inhibition sandwich binding assay, the blank values were determined in the absence of both biotinylated c-myc peptide and scFvs.

ScFv Immunohistochemical Analysis on Rabbit and Human Sections

Paraffin-embedded sections were prepared from rabbit and human arterial tissues. Briefly, sections of 10 μm thick were deparaffinized and re-hydrated before neutralizing endogenous peroxidase activity with 3% $H_2O_2/H_2O$ for 5 minutes. Non-specific binding was then blocked with 4% (w/v) BSA in PBS solution for 30 minutes at 20° C. Positive scFv fractions in direct TR-FRET binding assay were diluted in 2% BSA/PBS at final concentrations comprised between 2 and 16.5 μg/mL according to the clone production and incubated on tissue sections for 16 hours at 4° C. Following washings in PBS, a mix of 1/250 anti c-myc (Miltenyi Biotec, Paris, France) and 1/250 anti 6His (Roche Diagnostics) mAbs in 2% BSA/PBS were applied to the sections for 3 hours at 20° C. After washings, the sections were incubated with 1/500 horseradish peroxidase (HRP)-conjugated anti-mouse IgG (Immunotech, Marseille, France) for 1 hour at 20° C. The binding of secondary antibody was detected with DAB substrate kit (Vectastain ABC kit reagent, Vector Laboratories, Peterborough, UK), which yielded a yellow brown color reaction. After washings, the sections were dehydrated and mounted in DPX medium.

ScFv Competitive Binding Assay on Rabbit Atherosclerotic Aorta Sections

Specificity of H2.1 scFv binding on tissue sections was also assessed by a competitive binding assay in order to inhibit the signal generated by the biotinylated form of H2.1 scFv. Two hundred μg of scFv were biotinylated according to a molar ratio protein/biotin-XX SSE of 1:10 as described in the previous section. Fifty μg of biotin-H2.1 scFv were then incubated on atherosclerotic NZW rabbit sections with or without a four-fold excess of unlabeled H2.1 scFv in 2% BSA/PBS for 16 hours at 4° C. Following washings, biotinylated scFv binding was detected using 5 μg/mL of streptavidin-peroxidase conjugate (Vector Laboratories) and DAB substrate (Vector Laboratories).

Target Immunoprecipitation and Identification by Mass Spectrometry Analysis

Nickel-coated superparamagnetic beads (Ademtech, Pessac, France) were pre-washed three times with 500 μL of Binding Buffer (BB) (20 mmol/L Tris, pH 7; 500 mmol/L NaCl) and then incubated for 1 hour with 1 mg of rabbit atheromatous proteins solubilized in low stringent lysis buffer in order to get rid of nonspecific binding proteins. The supernatant free of nonspecific binding proteins was recovered and incubated with 10 μg of purified K3.1 scFv or of an irrelevant scFv for 16 hours at 4° C. under rotation. The next day, 20 μL of clean pre-washed superparamagnetic beads were added and incubated for a further 1 hour at 20° C. After three washings with 500 μL of BB, the immunoprecipitated complexes were eluted with 2×30 μL of elution buffer (20 mmol/L Tris-HCl, pH 7.5; 500 mmol/L NaCl; 100 mmol/L imidazole). The protein complexes were then separated using 10% SDS-PAGE under reducing conditions. The band was excised and submitted to trypsin digestion, followed by liquid chromatography-tandem mass spectrometry analysis (LC-MS/MS).

ELISA Binding Assay on Human CA-II

Ninety-six well ELISA microtiter plates (Greiner) were coated overnight, at 4° C., with 100 μL of human recombinant carbonic anhydrase II (Sigma-Aldrich, St Louis, USA) at a final concentration of 10 μg/mL, or bovine serum albumin at 50 μg/mL in carbonate buffer (NaHCO3/Na2CO3, 50 mmol/L, pH 9.6). All further reactions were carried out at room temperature. Following three washing steps with PBS-Tween 20 (0.5% Tween 20), 100 μL of purified K3.1 scFv at 10 μg/mL were added to each well. After a 2-h incubation and five washing steps, bound scFv was labeled with a mix of HRP-conjugated anti c-myc (diluted 1/1000, Miltenyi Biotech) and anti 6His (diluted 1/500, Roche Diagnostics) mAbs. After 1-h incubation and washing steps, color was developed with 100 μL of 3,3',5,5'-Tetramethylbenzidine (TMB) liquid substrate system for ELISA (Sigma) and the absorbance was read at 450 nm with an Infinite® F500 reader (Tecan, Lyon, France).

Magnetic Resonance Imaging

Rabbits were sedated using ketamine (25 mg/kg IM), xylazine (2 mg/kg IM) and butorphanol (0.12 mg/kg IM). Anesthesia was maintained during the MRI protocol with 2% isoflurane inhalation. Rabbits were positioned prone on the MRI table. Imaging was performed with a 0.2 T clinical MRI system (Siemens Open Viva, Erlangen, Germany). T1-axial images of the abdominal aorta were acquired with a spin-echo sequence including a black blood excitation pulse scheme with the following parameters: repetition time (TR): 400 ms, echo time (TE): 16 ms, section thickness: 5 mm, matrix: 128×128, field of view (FOV): 50×50 mm$^2$, acquisition time: 20 min 32 sec, number of averages (NA): 12. T1-coronal and sagittal images of the abdominal aorta were obtained with a turbo spin echo sequence with the following parameters: TR: 450 ms, TE: 24 ms, section thickness: 6 mm, matrix: 246×256, FOV: 180×180 mm$^2$, TA: 2 min 31 second NA: 2 (T1 coronal images) and TR: 450 ms, TE: 24 ms, section thickness: 4 mm, matrix: 246×256, FOV: 180×180 mm$^2$, acquisition time: 7 min 26 second, NA: 6 (T1 sagittal images).

Results

In Vivo Phage-scFvs Selection on Apoe$^{-/-}$ Mice

To select, from the highly diverse human antibody library, the human phage-scFvs able to home to atherosclerotic plaques, we used an ApoE$^{-/-}$ mouse model that develops advanced lesions mimicking the pathophysiological aspects of coronary artery disease observed in humans. For each biopanning round, three successive injections of five-minute circulation time each were performed in order to promote the chance for phage-scFvs of interest to reach and bind targets in the affected sections without being unspecifically adsorbed on the luminal surface of vascular endothelium cells, and to avoid their clearance from the blood by the reticuloendothelial system (FIG. 1). Furthermore, we reasoned that during the in vivo selection a subtractive procedure of the library takes place naturally at the unaffected sites.

To have access both to the endothelial cell surface binding phages and to the extravased and internalized phages, we independently recovered three fractions from aortic tissue (FIG. 1). From the second round of selection, the number of recovered colony forming units (cfu) from affected tissue markedly increased compared to the first round (FIG. 2).

The enrichments of selected phages after the third round of biopanning for F1, F2 and F3 fractions were respectively 100-, 10- and 5-fold higher than those recovered from the first round of selection, underlining the probable selection of specific phages against endothelial and sub-endothelial targets (Table 1).

TABLE 1

Selected clones after third round of panning and number of identical sequences found in each extracted fraction

| Clone | Round 3 | | | Final |
|---|---|---|---|---|
| | F1 | F2 | F3 | Frequency (%)* |
| H2.1 | 2 | 8 | 5 | 10 |
| C3.3 | 9 | 6 | 0 | 10 |
| K3.1 | 5 | 3 | 4 | 8 |
| F5.1 | 1 | 3 | 4 | 5.3 |
| I8.1 | 1 | 1 | 3 | 3.3 |
| K3.24 | 2 | 0 | 0 | 1.3 |

*The sequence frequency represents the number of identical sequences identified from the pool of sequenced clones from round 3.

Following the last two rounds of selection, the random sequencing of 150 clones (around 50 from each fraction) revealed three over-represented amino-acid sequences, representing for two of them (H2.1 and C3.3) 10% and for the third one (K3.1) 8% of the sequenced clones in the screen. Three other amino-acid sequences that appeared more than once were also reported (Table 1). None of the scFv bearing these sequences was detected in the clones from the second round of biopanning, suggesting that the in vivo selection pressure was too low to select scFvs with similar sequences from the first two biopanning rounds. Sequence analysis of these six scFvs using the IMGT/V-QUEST database revealed six unique sequences whose CDRH3 and CDRL3 loops were of variable amino-acid composition. Regarding the CDR lengths, the three dominant clones (H2.1, C3.3 and K3.1) showed a similarity both in CDRH3 length (3 residues) and CDRL3 length (10 residues), which represented the fifth representativity of CDRH3 and the first and the third of CDR3Lκ and CDR3Lλ, respectively, in the original library. The other clones displayed more variable CDRH3 lengths, whereas the CDRL3 loops systematically comprised 9 amino acids. Among the three dominant clones, H2.1 scFv was mostly found in the F2 fraction, C3.3 scFv clone was not detected in the F3 fraction and K3.1 scFv was equally distributed among all the fractions. Since the number of recovered identical clones in each fraction was low and because this number could increase between two successive fractions (as for instance H2.1 sequence between the F1 and F2 fractions in Table 1), cross-contaminations between fractions could be considered as minimal.

ScFv Purification and Inhibition of HTRF Sandwich Binding Signal

To have access to higher concentrations of antibody fragments, the six scFvs were produced in soluble form using a non-suppressor E. coli strain and were purified from the induced bacterial lysates by nickel chromatography affinity. To test the feasibility of detecting interactions between purified scFvs and atheromatous protein extracts, we developed a highly sensitive binding assay from HTRF technology. In this assay, the scFvs were investigated for their abilities to inhibit the positive HTRF sandwich signal generated by a biotinylated c-myc peptide (FIG. 3). In the absence of competitor, the positive sandwich signal was taken to be 100%. All the fractions recovered after scFv purification were incubated with the biotin-c-myc peptide, and the time course of competition was measured for 24 hours. The results showed that the highest concentrated fraction from each scFv was able to compete for the c-myc-tag by inhibiting the signal by 50 to 95% after 16 hours of incubation according to the purified clones. In these assays, final concentrations of scFvs were estimated between 5 and 170 nmol/L according to the clone production and purification. This set of experiments showed that purified scFvs could easily be detected in a HTRF assay and subsequently be used in a direct TR-FRET screening assay for their abilities to recognize atheromatous protein extracts.

TR-FRET Binding Assay Between scFvs and Rabbit Atheromatous Protein Extracts

Confronted with the limitations of the classic screening approaches for soluble tissue extracts or cell cultures, which are both time- and material-consuming, we set up a very sensitive TR-FRET screening method, based on the direct binding between purified scFvs and atherosclerotic tissue lysate. FRET signals require the close vicinity of two fluorophores, each recognizing one binding partner, which greatly limit the emission of non-specific signals. TR-FRET method combines standard FRET technology with the low background benefit of fluorescence (TRF) measurement based on extremely long-lived emission of lanthanide complexes as $Eu^{3+} \subset$ tris-bipyridine cryptate (Eu)K. Firstly, rabbit tissue proteins were solubilized in four different buffers comprising non-ionic and/or anionic detergents in order to access a wide panel of proteins. Every protein extract was then biotinylated according to three different molar ratios of proteins/biotin so as to yield a large degree of labeling. The totality of these reagents was pooled according to a 1:1 (v/v) ratio. To determine the feasibility of using the biotinylated proteins pool in the TR-FRET binding assay, we previously analyzed the ability of biotin-labeled proteins to inhibit the positive HTRF sandwich signal generated by the biotin-c-myc peptide. Final concentrations of biotinylated atheromatous proteins at 0.1 and 1 µg/mL were able to inhibit the signal by 80 and 100% respectively after 16 hours of incubation at 4° C. (data not shown).

To minimize the background signal, the acceptor fluorophore streptavidin-XL665 needs to be used in nanomolar concentrations. Direct TR-FRET binding assay was monitored on solid phase in order to eliminate uncomplexed biotinylated proteins to scFvs and thus avoid trapping of the fluorophore acceptors by the abundant and unspecific proteins. In these experimental conditions, streptavidin-XL665 could be used in the nanomolar range. The six purified scFvs were pre-adsorbed on wells and independently incubated with biotinylated protein extracts. After washing out unbound proteins and incubation with both fluorophore reporters, the time course of the assay revealed positive FRET signals for four scFvs, suggesting that they were able to recognize partners present within the protein soup (FIG. 4). In addition, no binding signal was reported on a biotinylated control protein (data not shown). F5.1 scFv was certainly not concentrated (3 µg/mL in the fraction) and pure enough (data not shown) to be detected in this assay. Conversely, the specificity of the assay was shown through the K3.24 scFv, highly purified and concentrated (100 µg/mL), that was strongly detected in the competitive HTRF assay but unable to generate a positive direct TR-FRET signal. Importantly, the DeltaF signals were not only proportional to the scFv concentration but also to the abundance of the cognate atheromatous antigen in the tissue extracts. These FRET signals were absent or very weak when the TR-FRET approach was achieved in liquid phase, without coating and washing steps (data not shown).

To further confirm the specificity of the FRET signal recorded on the atheromatous proteins, a new set of experiments was carried out in the presence of unlabeled protein extract used as competitor (FIGS. 5A and 5B). As expected, a dose-dependent inhibition was observed with unbiotinylated atherosclerotic proteins and a six-fold excess of proteins was able to quench the DeltaF binding values by approximately 75%, 80% and 60% for H2.1, I8.1 and K3.1 scFvs, respectively (FIG. 5A). Moreover, the same experiments performed with a six-fold excess of proteins extracted from untreated control rabbits also revealed an inhibition response but which was weaker, around 50%, 35% and 40% for H2.1, I8.1 and K3.1 scFvs respectively (FIG. 5B). These results suggested that scFvs recognized binding partners that were over-expressed in the lesional tissue of atheromatous rabbits relative to the tissue extracted from healthy rabbits.

Immunohistochemical Localization of scFvs on Rabbit and Human Aorta Sections

ScFvs were tested for their abilities to target ex vivo atherosclerotic sections obtained from thoracic aorta regions of hypercholesterolemic rabbits that underwent an angioplasty. Endovascular local injuries are well known to potentiate atherogenesis and to mimic the vulnerable plaque formation in humans. Deparaffinized sections were incubated with selected scFvs and the binding then revealed by immunohistochemistry. Positive scFvs in the direct TR-FRET assay were able to recognize the atheromatous sections and showed very specific staining patterns. Although a diffuse extracellular labeling was found within the intima, H2.1 and K3.1 scFvs stained intensively both an area rich in macrophage- and smooth muscle cell-derived foam cells under endothelium and a deeper area rich in necrotic cells adjacent to the internal elastic lamina in the advanced lesion. This staining was comparable to that observed with anti-macrophage RAM11 mAb. Unlike staining patterns obtained with H2.1 and K3.1 scFvs, I8.1 scFv stained mostly endothelium and superficial sub-endothelial layers, whereas a weak labeling was also detected in the deeper intimal layers and in the adventitia. An intense and specific staining within the lipid and necrotic core-rich regions was revealed with C3.3 scFv. Regarding the K3.24 scFv clone, there was no detectable binding through the section.

To further confirm the specificity of these clones, competitive binding assays on rabbit atherosclerotic sections were performed. Here, we illustrate the inhibition of biotinylated H2.1 scFv binding by a four-fold excess of its homologous unlabeled version. Revelation with the streptavidin-HRP conjugate showed a net decrease in staining compared to that obtained in the absence of competitor.

Standard NZW rabbit diets are not classically considered to be favorable for promoting the formation of atherosclerotic lesions. However, after a long life laboratory, rabbits are spontaneously susceptible to develop atheromatous lesions besides apparently healthy areas. We observed such modifications in our untreated control rabbits. In the atherosclerotic areas, staining with H2.1 scFv was predominantly associated with neointimal macrophage foam cells, although diffuse intimal labeling was also observed. Regarding I8.1 scFv, it mainly bound the endothelium cell surface of affected areas, even though diffuse and light staining was also seen through the intima. Interestingly, the aortic regions without atherosclerotic intimal lesions did not reveal any intense staining with H2.1 and I8.1 scFvs. Only a weak labeling was detected on some endothelial cells.

H2.1 and I8.1 scFvs were also incubated onto human sections of carotid and coronary arteries obtained from endarterectomy and cardiac transplant recipients, respectively. Even though both arteries showed well-developed plaques, the coronary artery showed a more advanced lesional stage. Both scFvs exhibited binding patterns very close to those observed on rabbit atheroma sections. The localization of H2.1 scFv binding occurred predominantly within the foam cell-rich regions in the carotid and in the necrotic lipid-rich areas of the coronary artery. I8.1 scFv staining was concentrated on the endothelium in the carotid and the coronary arteries, even though a weak staining was also detectable in necrotic cores of the coronary artery.

Taken altogether, these analyses confirmed that the selected scFvs were able to specifically home to atherosclerotic endothelial and sub-endothelial areas in rabbit and in human. The lack of binding within the non-lesional arterial areas of untreated rabbits suggested that recognized binding partners were certainly absent or under-expressed within the "normal" or pre-atherogenic intima.

CA-II Target Identification and ELISA Binding Assay of the K3.1 scFv

To identify the molecule recognized by purified K3.1 scFv, immunoprecipitation experiments using nickel superparamagnetic beads were performed to retain 6His-tagged scFvs complexed to antigens contained in the rabbit atherosclerotic protein lysate. Separated by SDS-PAGE and silver-stained, K3.1 scFv (~32 kDa) bound a protein with an apparent molecular mass of ~29 kDa, which did not appear in the controls performed in the absence of scFv or with irrelevant scFv. After band excision and mass spectrometry analysis, three dodecapeptides fully matched with cytosolic carbonic anhydrase isoenzyme II (CA-II), a protein of 29 kDa that seemed strongly to be the putative binding antigen recognized by the K3.1 scFv. Interestingly, this rabbit protein showed more than 85% homology with the corresponding human protein.

To further confirm the binding specificity of K3.1 scFv, an ELISA was performed on a commercial human recombinant CA-II antigen. Binding signals obtained on CA-II confirmed the immunoreactivity of K3.1 scFv with this target.

In Vivo Phage-scFvs Selection on a Rabbit Model of Atherosclerosis

To isolate phage-scFvs targeting atherosclerotic components of vulnerable plaques, we first developed a rabbit model of induced inflammation. In rabbits fed a high cholesterol diet, two kinds of surgery promoted the development of plaques reminiscent of human atherosclerotic lesions, in terms of cellular composition, patterns of lipid accumulation and growth characteristics. Before performing the in vivo phage display selection, it was crucial to know the state of development of the vulnerable plaques. To this end, we examined the atherosclerotic rabbit abdominal aorta with in vivo magnetic resonance imaging (MRI) and observed a thickened vessel wall and crescent-shaped plaques. The thickened intima, a hallmark of the pathology, is clearly visible on the sagittal slice. Plaques that protrude into the lumen of the vessel are visible.

Histology proved that the protocol indeed induced highly vulnerable plaques with foam cells, necrotic cores and cholesterol. The intima is thickened and highly disorganized; macrophages and collagen fibers are interspersed as demonstrated by staining with Masson's trichrome. Masson's trichrome is a three-color staining protocol, well suited for distinguishing cells from surrounding connective tissue. Connective tissue is stained blue, nuclei are stained dark red/purple, and cytoplasm is stained red/pink. Foamy cells derived from macrophages as well as from smooth muscle cells (SMS) are the major cell types in atheroma. Foam cells, necrotic core and cholesterol crystals are easily distinguishable components of the vulnerable plaque, commonly described in the literature.

The semi-synthetic scFv-fragment library, designed and constructed by Philibert et al., was injected into the marginal ear vein of the rabbit. To ensure distribution of phage-scFvs in the tissues, we used an injection pump that provided constant flow and a circulation time optimized to 30 min. These two factors combined allow both a saturation of non specific sites with phages not expressing scFv fragments (more than 90% of the total population) and a continuous supply of phage-scFvs, thus opposing clearance and catabolism via the major organs of the RES. Moreover, in vivo selection implies de facto that a negative selection occurs against the areas not affected by the disease. The animals were then sacrificed and the aortas extracted from the aortic arch to the iliac bifurcation.

In previous in vivo selections, performed in ApoE$^{-/-}$ mice, we showed that the intravenous injection of phage-display scFv libraries permits the identification of candidates homing to atherosclerotic lesions not only in sites accessible to blood but also inside the lesions. Like tumors that have a vasculature much different from that of normal organs, atherosclerotic lesions have leaky endothelial cells. We thus hypothesized that phage-scFvs may directly contact sub-endothelial components and lesion-invading cells via the blood vessel or the vasa vasorum. We thus proceeded by a multi-step recovery and isolated phage-scFvs from three fractions in atherosclerotic tissue: the endothelium cell surface-bound phages-scFv (fraction F1), the intra-tissular fraction (F2) and the phages-scFv internalized in cells (F3). This is not a clear-cut recovery, which means that the intra-tissular fraction may contain tightly surface-bound phages-scFv and that the F3 fraction may be a sum of tightly bound, matrix-entrapped or real internalized phage-scFvs, probably captured in foam cells which constitute the main cellular components of the intima. This multi-step approach was performed around the idea of increasing phage-scFv recovery from the whole thickened intima, rich in targets overexpressed during the progression of the pathology. Most in vivo biopanning procedures were so far limited to the targets covering the vasculature surface.

We performed only two rounds of in vivo biopanning in order to allow identification of in vivo-enriched binders without compromising diversity. It has been reported multiple selection rounds decreases the complexity of the selected repertoire. At each round, we independently recovered F1, F2 and F3 fractions from diseased aortic tissue. From the second round of selection, we noted that the number of recovered phage-scFvs from affected tissue in F1, F2 and F3 fractions increased compared to the first round. The number of recovered phages after the second round of selection was $1.13 \times 10^5$, $1.15 \times 10^5$ and 500 cfu for fractions F1, F2 and F3 respectively. In other words, the number of output phage-scFvs normalized for an input of $10^{12}$ was increased by a factor 5 for the fractions F1 and F2, and by a factor 50 for the fraction F3. The fact that we not only show an enrichment in the fraction F1 but also in fractions F2 and F3, (with an even greater enrichment in the fraction F3), suggests to us that the implemented technology has led to the in vivo selection of scFvs able to reach subjacent lesional tissue layers and to be internalized within cells invading the intima.

REFERENCES

Shaw P. X. et al., Arterioscler. Thromb. Vasc. Biol., 21:1333-1339, 2001
Gamble W., Journal of Theoretical Biology 239, 16-21, 2006
Philibert P. et al., BMC Biotechnol., 7:81, 2007
Oksala N. et al., Annals of Medicine, 42:360-370, 2010
Briley-Saebo et al., J. Am. Coll. Cardiol., 2011
Matter C M et al., Circ Res., 95:1225-1233, 2004
WO2004107368

The invention claimed is:

1. Antibody specifically binding to atherosclerosis lesions wherein said antibody or antibody fragment comprises at least a VH CDR1 comprising the amino acid sequence of SEQ ID No.1, a VH CDR2 comprising the amino acid sequence of SEQ ID No.2, a VL CDR1 comprising the amino acid sequence of SEQ ID No.3 and a VL CDR2 comprising the amino acid sequence of SEQ ID No.4; and comprising at least:
 a VH CDR3 comprising the amino acid sequence of SEQ ID No.5 and a VL CDR3 comprising the amino acid sequence of SEQ ID No.6, or
 a VH CDR3 comprising the amino acid sequence of SEQ ID No.10 and a VL CDR3 comprising the amino acid sequence of SEQ ID No.11, or
 a VH CDR3 comprising the amino acid sequence of SEQ ID No.15 and a VL CDR3 comprising the amino acid sequence of SEQ ID No.16, or
 a VH CDR3 comprising the amino acid sequence of SEQ ID No.20 and a VL CDR3 comprising the amino acid sequence of SEQ ID No.21.

2. The antibody according to claim 1 comprising at least:
 a VH domain comprising the amino acid sequence of SEQ ID No.7 and a VL domain comprising the amino acid sequence of SEQ ID No.8, or
 a VH domain comprising the amino acid sequence of SEQ ID No.12 and a VL domain comprising the amino acid sequence of SEQ ID No.13, or
 a VH domain comprising the amino acid sequence of SEQ ID No.17 and a VL domain comprising the amino acid sequence of SEQ ID No.18, or
 a VH domain comprising the amino acid sequence of SEQ ID No.22 and a VL domain comprising the amino acid sequence of SEQ ID No.23.

3. The antibody according to claim 1 or 2 wherein the antibody is a recombinant human IgG.

4. The antibody according to claim 1 or 2 wherein the antibody is a recombinant human Fab'2, recombinant human scFv-Fab'2 or recombinant human scFv-Fc.

5. The antibody according to claim 1 or 2 wherein the antibody is a recombinant human scFv antibody.

6. The antibody according to claim 1 or 2 wherein the antibody is a recombinant human scFv antibody selected in the group consisting of:
 the scFv antibody of SEQ ID No.9,
 the scFV antibody of SEQ ID No.14,
 the scFV antibody of SEQ ID No.19,
 the scFv antibody of SEQ ID No.24.

7. A polynucleotide encoding an antibody according to claim 1.

8. A recombinant host cell comprising a polynucleotide encoding an antibody according to claim 1.

9. The antibody according to claim 1, 2 or 6 wherein said antibody is labeled for in vivo imaging.

10. The antibody according to claim 9 wherein the antibody is labeled with a radiotracer for Nuclear Imaging or wherein the antibody is labeled with a magnetic contrast agent for Magnetic Resonance Imaging.

11. A method for in vivo imaging of atherosclerosis lesions in a patient comprising visualization of the atherosclerosis lesions by detection of a labeled antibody previously administered to the patient wherein the antibody is an antibody according to claim 9.

12. The method according to claim 11 wherein the antibody is labeled with a radiotracer and visualization of the atherosclerosis lesions is performed by Nuclear Imaging.

13. The method according to claim 11 wherein the antibody is labeled with a contrast agent and visualization of the atherosclerosis lesions is performed by Magnetic Resonance Imaging.

14. A method for in vivo imaging of atherosclerosis lesions in a patient comprising the following steps:
 a) Intravenous injection of an antibody according to claim 9 labeled for in vivo imaging into the patient,
 b) Visualization of the atherosclerosis lesions by detection of the labeled antibody of step a) in the patient.

15. An antibody specifically binding to atherosclerosis lesions wherein said antibody or antibody fragment comprises at least a VH CDR1 comprising the amino acid sequence of SEQ ID No.1, a VH CDR2 comprising the amino acid sequence of SEQ ID No.2, a VL CDR1 comprising the amino acid sequence of SEQ ID No.3 and a VL CDR2 comprising the amino acid sequence of SEQ ID No.4; and comprising at least:
 a VH CDR3 comprising the amino acid sequence of SEQ ID No.25 and a VL CDR3 comprising the amino acid sequence of SEQ ID No.26, or
 a VH CDR3 comprising the amino acid sequence of SEQ ID No.30 and a VL CDR3 comprising the amino acid sequence of SEQ ID No.31, or
 a VH CDR3 comprising the amino acid sequence of SEQ ID No.35 and a VL CDR3 comprising the amino acid sequence of SEQ ID No.36.

16. The antibody according to claim 15 comprising at least:
 a VH domain comprising the amino acid sequence of SEQ ID No.27 and a VL domain comprising the amino acid sequence of SEQ ID No.28, or
 a VH domain comprising the amino acid sequence of SEQ ID No.32 and a VL domain comprising the amino acid sequence of SEQ ID No.33, or
 a VH domain comprising the amino acid sequence of SEQ ID No.37 and a VL domain comprising the amino acid sequence of SEQ ID No.38.

17. The antibody according to claim 15 or 16 wherein the antibody is a recombinant human IgG.

18. The antibody according to claim 15 or 16 wherein the antibody is a recombinant human Fab'2, recombinant human scFv-Fab'2 or recombinant human scFv-Fc.

19. The antibody according to claim 15 or 16 wherein the antibody is a recombinant human scFv antibody.

20. The antibody according to claim 15 or 16 wherein the antibody is a recombinant human scFv antibody selected in the group consisting of:
 the scFv antibody of SEQ ID No.29,
 the scFv antibody of SEQ ID No.34, and
 the scFv antibody of SEQ ID No.39.

21. A polynucleotide encoding an antibody according to claim 15.

22. A recombinant host cell comprising a polynucleotide encoding an antibody according to claim 15.

23. The antibody according to claim 15, 16 or 20 wherein said antibody is labeled for in vivo imaging.

24. The antibody according to claim 23 wherein the antibody is labeled with a radiotracer for Nuclear Imaging or wherein the antibody is labeled with a magnetic contrast agent for Magnetic Resonance Imaging.

25. A method for in vivo imaging of atherosclerosis lesions in a patient comprising visualization of the atherosclerosis lesions by detection of a labeled antibody previously administered to the patient wherein the antibody is an antibody according to claim 23.

26. The method according to claim 25 wherein the antibody is labeled with a radiotracer and visualization of the atherosclerosis lesions is performed by Nuclear Imaging.

27. The method according to claim 25 wherein the antibody is labeled with a contrast agent and visualization of the atherosclerosis lesions is performed by Magnetic Resonance Imaging.

28. A method for in vivo imaging of atherosclerosis lesions in a patient comprising the following steps:
   e) Intravenous injection of an antibody according to claim 23 labeled for in vivo imaging into the patient,
   f) Visualization of the atherosclerosis lesions by detection of the labeled antibody of step a) in the patient.

* * * * *

SEQUENCE LISTING

```
<160> NUMBER OF SEQ ID NOS: 40

<210> SEQ ID NO 1
<211> LENGTH: 8
<212> TYPE: PRT
<213> ORGANISM: Homo sapiens

<400> SEQUENCE: 1

Gly Phe Thr Phe Ser Asn Tyr Ser
1               5

<210> SEQ ID NO 2
<211> LENGTH: 8
<212> TYPE: PRT
<213> ORGANISM: Homo sapiens

<400> SEQUENCE: 2

Ile Ser Gly Ser Ser Arg Tyr Ile
1               5

<210> SEQ ID NO 3
<211> LENGTH: 9
<212> TYPE: PRT
<213> ORGANISM: Homo sapiens
```

```
<400> SEQUENCE: 3

Ser Ser Asp Val Gly Gly Tyr Asn Tyr
1               5

<210> SEQ ID NO 4
<211> LENGTH: 3
<212> TYPE: PRT
<213> ORGANISM: Homo sapiens

<400> SEQUENCE: 4

Glu Asp Ser
1

<210> SEQ ID NO 5
<211> LENGTH: 15
<212> TYPE: PRT
<213> ORGANISM: Homo sapiens

<400> SEQUENCE: 5

Val Arg Gly Glu Gly Leu Tyr Ser Gly Ser Tyr Asn Leu His Tyr
1               5                   10                  15

<210> SEQ ID NO 6
<211> LENGTH: 10
<212> TYPE: PRT
<213> ORGANISM: Homo sapiens

<400> SEQUENCE: 6

Gly Thr Pro Asn Thr His Ala Leu Trp Val
1               5                   10

<210> SEQ ID NO 7
<211> LENGTH: 122
<212> TYPE: PRT
<213> ORGANISM: Homo sapiens

<400> SEQUENCE: 7

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Glu Gly Leu Tyr Ser Gly Ser Tyr Asn Leu His Tyr Trp
            100                 105                 110

Gly Arg Gly Thr Leu Val Thr Val Ser Ser
        115                 120

<210> SEQ ID NO 8
<211> LENGTH: 108
<212> TYPE: PRT
<213> ORGANISM: Homo sapiens
```

-continued

<400> SEQUENCE: 8

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Asp Ser Lys Arg Pro Ser Gly Val Ser Asn Arg Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Phe Cys Gly Thr Pro Asn Thr His Ala
                85                  90                  95

Leu Trp Val Phe Gly Gly Gly Thr Lys Leu Ala Val
            100                 105

<210> SEQ ID NO 9
<211> LENGTH: 246
<212> TYPE: PRT
<213> ORGANISM: Artificial Sequence
<220> FEATURE:
<223> OTHER INFORMATION: scFv recombinant antibody

<400> SEQUENCE: 9

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Glu Gly Leu Tyr Ser Gly Ser Tyr Asn Leu His Tyr Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Ser Gln Ser Val Leu Thr Gln Pro
    130                 135                 140

Ala Ser Val Ser Gly Ser Pro Gly Gln Ser Ile Thr Ile Ser Cys Ala
145                 150                 155                 160

Gly Thr Ser Ser Asp Val Gly Gly Tyr Asn Tyr Val Ser Trp Tyr Gln
                165                 170                 175

Gln His Pro Gly Lys Ala Pro Lys Leu Met Ile Tyr Glu Asp Ser Lys
            180                 185                 190

Arg Pro Ser Gly Val Ser Asn Arg Phe Ser Gly Ser Lys Ser Gly Asn
        195                 200                 205

Thr Ala Ser Leu Thr Ile Ser Gly Leu Gln Ala Glu Asp Glu Ala Asp
    210                 215                 220

```
Tyr Phe Cys Gly Thr Pro Asn Thr His Ala Leu Trp Val Phe Gly Gly
225                 230                 235                 240

Gly Thr Lys Leu Ala Val
            245

<210> SEQ ID NO 10
<211> LENGTH: 15
<212> TYPE: PRT
<213> ORGANISM: Homo sapiens

<400> SEQUENCE: 10

Val Arg Gly Ile Asp Gly Gly Gly Trp Asn Tyr Phe Asp His
1               5                   10                  15

<210> SEQ ID NO 11
<211> LENGTH: 10
<212> TYPE: PRT
<213> ORGANISM: Homo sapiens

<400> SEQUENCE: 11

Arg Gln Pro Ser Asn Ser Pro Pro Leu Asn
1               5                   10

<210> SEQ ID NO 12
<211> LENGTH: 122
<212> TYPE: PRT
<213> ORGANISM: Homo sapiens

<400> SEQUENCE: 12

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Ile Asp Gly Gly Gly Trp Asn Tyr Phe Asp His Trp
            100                 105                 110

Gly Arg Gly Thr Leu Val Thr Val Ser Ser
        115                 120

<210> SEQ ID NO 13
<211> LENGTH: 109
<212> TYPE: PRT
<213> ORGANISM: Homo sapiens

<400> SEQUENCE: 13

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Asp Ser Lys Arg Pro Ser Gly Val Ser Asn Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Arg Gln Pro Ser Asn Ser
                 85                  90                  95

Pro Pro Leu Asn Phe Gly Gly Gly Thr Lys Leu Ala Val
            100                 105

<210> SEQ ID NO 14
<211> LENGTH: 246
<212> TYPE: PRT
<213> ORGANISM: Artificial Sequence
<220> FEATURE:
<223> OTHER INFORMATION: scFv recombinant antibody

<400> SEQUENCE: 14

Glu Val Gln Leu Val Glu Ser Gly Gly Ser Leu Val Lys Pro Gly Gly
  1               5                  10                  15

Ser Leu Arg Leu Ser Cys Ala Ala Ser Gly Phe Thr Phe Ser Asn Tyr
             20                  25                  30

Ser Met Asn Trp Val Arg Gln Ala Pro Gly Lys Gly Leu Glu Trp Ile
         35                  40                  45

Ser Ser Ile Ser Gly Ser Ser Arg Tyr Ile Tyr Tyr Ala Asp Phe Val
 50                  55                  60

Lys Gly Arg Phe Thr Ile Ser Arg Asp Asn Ala Thr Asn Ser Leu Tyr
 65                  70                  75                  80

Leu Gln Met Asn Ser Leu Arg Ala Glu Asp Thr Ala Val Tyr Tyr Cys
             85                  90                  95

Val Arg Gly Ile Asp Gly Gly Gly Trp Asn Tyr Phe Asp His Trp
            100                 105                 110

Gly Arg Gly Thr Leu Val Thr Val Ser Ser Gly Gly Gly Ser Gly
            115                 120                 125

Gly Gly Gly Ser Gly Gly Gly Ser Gln Ser Val Leu Thr Gln Pro
            130                 135                 140

Ala Ser Val Ser Gly Ser Pro Gly Gln Ser Ile Thr Ile Ser Cys Ala
145                 150                 155                 160

Gly Thr Ser Ser Asp Val Gly Gly Tyr Asn Tyr Val Ser Trp Tyr Gln
                165                 170                 175

Gln His Pro Gly Lys Ala Pro Lys Leu Met Ile Tyr Glu Asp Ser Lys
            180                 185                 190

Arg Pro Ser Gly Val Ser Asn Arg Phe Ser Gly Ser Lys Ser Gly Asn
        195                 200                 205

Thr Ala Ser Leu Thr Ile Ser Gly Leu Gln Ala Glu Asp Glu Ala Asp
        210                 215                 220

Tyr Tyr Cys Arg Gln Pro Ser Asn Ser Pro Pro Leu Asn Phe Gly Gly
225                 230                 235                 240

Gly Thr Lys Leu Ala Val
            245

<210> SEQ ID NO 15
<211> LENGTH: 15
<212> TYPE: PRT
<213> ORGANISM: Homo sapiens

<400> SEQUENCE: 15

Val Arg Gly Gly Val Asp Ser Ser Gly Asp Asn Cys Phe Asp Leu
  1               5                  10                  15
```

```
<210> SEQ ID NO 16
<211> LENGTH: 10
<212> TYPE: PRT
<213> ORGANISM: Homo sapiens

<400> SEQUENCE: 16

Thr Ser Tyr Gly Ser Gly Ala Thr Leu Val
1               5                   10

<210> SEQ ID NO 17
<211> LENGTH: 122
<212> TYPE: PRT
<213> ORGANISM: Homo sapiens

<400> SEQUENCE: 17

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Gly Val Asp Ser Ser Gly Asp Asn Cys Phe Asp Leu Trp
            100                 105                 110

Gly Arg Gly Thr Leu Val Thr Val Ser Ser
        115                 120

<210> SEQ ID NO 18
<211> LENGTH: 109
<212> TYPE: PRT
<213> ORGANISM: Homo sapiens

<400> SEQUENCE: 18

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Asp Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Cys Thr Ser Tyr Gly Ser Gly
                85                  90                  95

Ala Thr Leu Val Phe Gly Gly Gly Thr Lys Leu Ala Val
            100                 105

<210> SEQ ID NO 19
<211> LENGTH: 246
<212> TYPE: PRT
<213> ORGANISM: Artificial Sequence
<220> FEATURE:
<223> OTHER INFORMATION: scFv recombinant antibody
```

<400> SEQUENCE: 19

Glu Val Gln Leu Val Glu Ser Gly Gly Ser Leu Val Lys Pro Gly Gly
1               5                   10                  15
Ser Leu Arg Leu Ser Cys Ala Ala Ser Gly Phe Thr Phe Ser Asn Tyr
            20                  25                  30
Ser Met Asn Trp Val Arg Gln Ala Pro Gly Lys Gly Leu Glu Trp Ile
        35                  40                  45
Ser Ser Ile Ser Gly Ser Ser Arg Tyr Ile Tyr Tyr Ala Asp Phe Val
    50                  55                  60
Lys Gly Arg Phe Thr Ile Ser Arg Asp Asn Ala Thr Asn Ser Leu Tyr
65                  70                  75                  80
Leu Gln Met Asn Ser Leu Arg Ala Glu Asp Thr Ala Val Tyr Tyr Cys
                85                  90                  95
Val Arg Gly Gly Val Asp Ser Ser Gly Asp Asn Cys Phe Asp Leu Trp
            100                 105                 110
Gly Arg Gly Thr Leu Val Thr Val Ser Ser Gly Gly Gly Gly Ser Gly
        115                 120                 125
Gly Gly Gly Ser Gly Gly Gly Ser Gln Ser Val Leu Thr Gln Pro
    130                 135                 140
Ala Ser Val Ser Gly Ser Pro Gly Gln Ser Ile Thr Ile Ser Cys Ala
145                 150                 155                 160
Gly Thr Ser Ser Asp Val Gly Gly Tyr Asn Tyr Val Ser Trp Tyr Gln
                165                 170                 175
Gln His Pro Gly Lys Ala Pro Lys Leu Met Ile Tyr Glu Asp Ser Lys
            180                 185                 190
Arg Pro Ser Gly Val Ser Asn Arg Phe Ser Gly Ser Lys Ser Gly Asn
        195                 200                 205
Thr Ala Ser Leu Thr Ile Ser Gly Leu Gln Ala Glu Asp Glu Ala Asp
    210                 215                 220
Tyr Tyr Cys Thr Ser Tyr Gly Ser Gly Ala Thr Leu Val Phe Gly Gly
225                 230                 235                 240
Gly Thr Lys Leu Ala Val
                245

<210> SEQ ID NO 20
<211> LENGTH: 17
<212> TYPE: PRT
<213> ORGANISM: Homo sapiens

<400> SEQUENCE: 20

Val Arg Asn Ser Phe Tyr Ala Ser Trp Ser Lys Asp Tyr Ser Met Glu
1               5                   10                  15
Ile

<210> SEQ ID NO 21
<211> LENGTH: 9
<212> TYPE: PRT
<213> ORGANISM: Homo sapiens

<400> SEQUENCE: 21

Gln Ser Trp Ala Ser Arg Ile Asn Ile
1               5

<210> SEQ ID NO 22
<211> LENGTH: 124
<212> TYPE: PRT
<213> ORGANISM: Homo sapiens

<400> SEQUENCE: 22

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asn Ser Phe Tyr Ala Ser Trp Ser Lys Asp Tyr Ser Met Glu
            100                 105                 110

Ile Trp Gly Arg Gly Thr Leu Val Thr Val Ser Ser
        115                 120

<210> SEQ ID NO 23
<211> LENGTH: 108
<212> TYPE: PRT
<213> ORGANISM: Homo sapiens

<400> SEQUENCE: 23

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Asp Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Ala Ser Arg
                85                  90                  95

Ile Asn Ile Phe Gly Gly Gly Thr Lys Leu Ala Val
            100                 105

<210> SEQ ID NO 24
<211> LENGTH: 247
<212> TYPE: PRT
<213> ORGANISM: Artificial Sequence
<220> FEATURE:
<223> OTHER INFORMATION: scFv recombinant antibody

<400> SEQUENCE: 24

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

```
Leu Gln Met Asn Ser Leu Arg Ala Glu Asp Thr Ala Val Tyr Tyr Cys
             85                  90                  95

Val Arg Asn Ser Phe Tyr Ala Ser Trp Ser Lys Asp Tyr Ser Met Glu
        100                 105                 110

Ile Trp Gly Arg Gly Thr Leu Val Thr Val Ser Ser Gly Gly Gly Gly
    115                 120                 125

Ser Gly Gly Gly Gly Ser Gly Gly Gly Gly Ser Gln Ser Val Leu Thr
130                 135                 140

Gln Pro Ala Ser Val Ser Gly Ser Pro Gly Gln Ser Ile Thr Ile Ser
145                 150                 155                 160

Cys Ala Gly Thr Ser Ser Asp Val Gly Gly Tyr Asn Tyr Val Ser Trp
                165                 170                 175

Tyr Gln Gln His Pro Gly Lys Ala Pro Lys Leu Met Ile Tyr Glu Asp
            180                 185                 190

Ser Lys Arg Pro Ser Gly Val Ser Asn Arg Phe Ser Gly Ser Lys Ser
        195                 200                 205

Gly Asn Thr Ala Ser Leu Thr Ile Ser Gly Leu Gln Ala Glu Asp Glu
    210                 215                 220

Ala Asp Tyr Tyr Cys Gln Ser Trp Ala Ser Arg Ile Asn Ile Phe Gly
225                 230                 235                 240

Gly Gly Thr Lys Leu Ala Val
                245

<210> SEQ ID NO 25
<211> LENGTH: 10
<212> TYPE: PRT
<213> ORGANISM: Homo sapiens

<400> SEQUENCE: 25

Val Arg Gly Gly Gly Ser Glu Leu Gly Asp
1               5                   10

<210> SEQ ID NO 26
<211> LENGTH: 9
<212> TYPE: PRT
<213> ORGANISM: Homo sapiens

<400> SEQUENCE: 26

Gln Lys Tyr Asn Asn Thr Thr His Ile
1               5

<210> SEQ ID NO 27
<211> LENGTH: 117
<212> TYPE: PRT
<213> ORGANISM: Homo sapiens

<400> SEQUENCE: 27

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80
```

Leu Gln Met Asn Ser Leu Arg Ala Glu Asp Thr Ala Val Tyr Tyr Cys
                    85                  90                  95

Val Arg Gly Gly Gly Ser Glu Leu Gly Asp Trp Gly Arg Gly Thr Leu
                100                 105                 110

Val Thr Val Ser Ser
            115

<210> SEQ ID NO 28
<211> LENGTH: 110
<212> TYPE: PRT
<213> ORGANISM: Homo sapiens

<400> SEQUENCE: 28

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Asp Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Lys Tyr Asn Asn Thr
                85                  90                  95

Thr His Ile Phe Gly Gly Gly Thr Lys Leu Ala Val Leu Gly
                100                 105                 110

<210> SEQ ID NO 29
<211> LENGTH: 242
<212> TYPE: PRT
<213> ORGANISM: Homo sapiens

<400> SEQUENCE: 29

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
                20                  25                  30

Ser Met Asn Trp Val Arg Gln Ala Pro Gly Lys Gly Leu Glu Trp Ile
            35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Gly Gly Gly Ser Glu Leu Gly Asp Trp Gly Arg Gly Thr Leu
                100                 105                 110

Val Thr Val Ser Ser Gly Gly Gly Gly Ser Gly Gly Gly Gly Ser Gly
            115                 120                 125

Gly Gly Gly Ser Gln Ser Val Leu Thr Gln Pro Ala Ser Val Ser Gly
        130                 135                 140

Ser Pro Gly Gln Ser Ile Thr Ile Ser Cys Ala Gly Thr Ser Ser Asp
145                 150                 155                 160

Val Gly Gly Tyr Asn Tyr Val Ser Trp Tyr Gln Gln His Pro Gly Lys
                165                 170                 175

```
Ala Pro Lys Leu Met Ile Tyr Glu Asp Ser Lys Arg Pro Ser Gly Val
            180                 185                 190

Ser Asn Arg Phe Ser Gly Ser Lys Ser Gly Asn Thr Ala Ser Leu Thr
            195                 200                 205

Ile Ser Gly Leu Gln Ala Glu Asp Glu Ala Asp Tyr Tyr Cys Gln Lys
            210                 215                 220

Tyr Asn Asn Thr Thr His Ile Phe Gly Gly Thr Lys Leu Ala Val
225                 230                 235                 240

Leu Gly

<210> SEQ ID NO 30
<211> LENGTH: 16
<212> TYPE: PRT
<213> ORGANISM: Homo sapiens

<400> SEQUENCE: 30

Val Arg Glu Gly Arg Trp Pro Thr Val Asn Glu Asp Cys Leu Asp His
1               5                   10                  15

<210> SEQ ID NO 31
<211> LENGTH: 10
<212> TYPE: PRT
<213> ORGANISM: Homo sapiens

<400> SEQUENCE: 31

Ser Ser Tyr Thr Thr Arg Ser Thr Arg Val
1               5                   10

<210> SEQ ID NO 32
<211> LENGTH: 123
<212> TYPE: PRT
<213> ORGANISM: Homo sapiens

<400> SEQUENCE: 32

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
            35                  40                  45

Ser Ser Ile Ser Gly Ser Ser Arg Tyr Ile Tyr Tyr Ala Asp Phe Val
        50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Arg Trp Pro Thr Val Asn Glu Asp Cys Leu Asp His
            100                 105                 110

Trp Gly Arg Gly Thr Leu Val Thr Val Ser Ser
            115                 120

<210> SEQ ID NO 33
<211> LENGTH: 111
<212> TYPE: PRT
<213> ORGANISM: Homo sapiens
```

```
<400> SEQUENCE: 33

Gln Ser Val Leu Thr Gln Pro Ala Ser Val Ser Gly Ser Pro Gly Gln
1               5                   10                  15

Ser Ile Thr Ile Ser Cys Ala Gly Ala Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Asp Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Ala Val Leu Gly
            100                 105                 110

<210> SEQ ID NO 34
<211> LENGTH: 249
<212> TYPE: PRT
<213> ORGANISM: Homo sapiens

<400> SEQUENCE: 34

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Arg Trp Pro Thr Val Asn Gly Asp Cys Leu Asp His
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Gly Ser Gln Ser Val Leu Thr Gln
    130                 135                 140

Pro Ala Ser Val Ser Gly Ser Pro Gly Gln Ser Ile Thr Ile Ser Cys
145                 150                 155                 160

Ala Gly Ala Ser Ser Asp Val Gly Gly Tyr Asn Tyr Val Ser Trp Tyr
                165                 170                 175

Gln Gln His Pro Gly Lys Ala Pro Lys Leu Met Ile Tyr Glu Asp Ser
            180                 185                 190

Lys Arg Pro Ser Gly Val Ser Asn Arg Phe Ser Gly Ser Lys Ser Gly
        195                 200                 205

Asn Thr Ala Ser Leu Thr Ile Ser Gly Leu Gln Ala Glu Asp Glu Ala
    210                 215                 220

Asp Tyr Tyr Cys Ser Ser Tyr Thr Thr Arg Ser Thr Arg Val Phe Gly
225                 230                 235                 240

Gly Gly Thr Lys Leu Ala Val Leu Gly
                245
```

```
<210> SEQ ID NO 35
<211> LENGTH: 15
<212> TYPE: PRT
<213> ORGANISM: Homo sapiens

<400> SEQUENCE: 35

Val Arg Glu Gly Ser Arg Trp Gly Gly Tyr Asp Gly Phe Asp Tyr
1               5                   10                  15

<210> SEQ ID NO 36
<211> LENGTH: 10
<212> TYPE: PRT
<213> ORGANISM: Homo sapiens

<400> SEQUENCE: 36

Ser Ser Tyr Thr Thr Arg Ser Thr Arg Val
1               5                   10

<210> SEQ ID NO 37
<211> LENGTH: 122
<212> TYPE: PRT
<213> ORGANISM: Homo sapiens

<400> SEQUENCE: 37

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Ser Arg Trp Gly Gly Tyr Asp Gly Phe Asp Tyr Trp
            100                 105                 110

Gly Arg Gly Thr Leu Val Thr Val Ser Ser
        115                 120

<210> SEQ ID NO 38
<211> LENGTH: 111
<212> TYPE: PRT
<213> ORGANISM: Homo sapiens

<400> SEQUENCE: 38

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Asn Tyr Val Ser Trp Tyr Gln Gln His Pro Gly Lys Ala Pro Arg Leu
        35                  40                  45

Met Ile Tyr Glu Asp Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80
```

```
Gln Ala Glu Asp Glu Ala Asp Tyr Tyr Cys Ser Ser Tyr Thr Thr Arg
                85                  90                  95

Ser Thr Arg Val Phe Gly Gly Gly Thr Lys Leu Ala Val Leu Gly
            100                 105                 110
```

<210> SEQ ID NO 39
<211> LENGTH: 248
<212> TYPE: PRT
<213> ORGANISM: Homo sapiens

<400> SEQUENCE: 39

```
Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Ile
        35                  40                  45

Ser Ser Ile Ser Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Ser Arg Trp Gly Gly Tyr Asp Gly Phe Asp Tyr Trp
            100                 105                 110

Gly Arg Gly Thr Leu Val Thr Val Ser Ser Gly Gly Gly Gly Ser Gly
        115                 120                 125

Gly Gly Gly Ser Gly Gly Gly Ser Gln Ser Val Leu Thr Gln Pro
    130                 135                 140

Ala Ser Val Ser Gly Ser Pro Gly Gln Ser Ile Thr Ile Ser Cys Ala
145                 150                 155                 160

Gly Thr Ser Ser Asp Val Gly Gly Tyr Asn Tyr Val Ser Trp Tyr Gln
                165                 170                 175

Gln His Pro Gly Lys Ala Pro Arg Leu Met Ile Tyr Glu Asp Ser Lys
            180                 185                 190

Arg Pro Ser Gly Val Ser Asn Arg Phe Ser Gly Ser Lys Ser Gly Asn
        195                 200                 205

Thr Ala Ser Leu Thr Ile Ser Gly Leu Gln Ala Glu Asp Glu Ala Asp
    210                 215                 220

Tyr Tyr Cys Ser Ser Tyr Thr Thr Arg Ser Thr Arg Val Phe Gly Gly
225                 230                 235                 240

Gly Thr Lys Leu Ala Val Leu Gly
                245
```

<210> SEQ ID NO 40
<211> LENGTH: 17
<212> TYPE: DNA
<213> ORGANISM: Artificial
<220> FEATURE:
<223> OTHER INFORMATION: LMB3 primer

<400> SEQUENCE: 40
caggaaacag ctatgac                                                    17